United States Patent (10) Patent No.: US 10,925,831 B2
Bierbach et al. (45) Date of Patent: Feb. 23, 2021

(54) LIPOSOMAL FORMULATIONS OF PLATINUM-ACRIDINE ANTICANCER AGENTS AND METHODS THEREOF

(71) Applicant: Wake Forest University, Winston-Salem, NC (US)

(72) Inventors: Ulrich Bierbach, Winston-Salem, NC (US); Song Ding, Durham, NC (US); Christopher L. Hackett, Hagerstown, MD (US)

(73) Assignee: Wake Forest University, Winston-Salem, NC (US)

( * ) Notice: Subject to any disclaimer, the term of this patent is extended or adjusted under 35 U.S.C. 154(b) by 30 days.

(21) Appl. No.: 16/114,431

(22) Filed: Aug. 28, 2018

(65) Prior Publication Data
US 2019/0060234 A1 Feb. 28, 2019

Related U.S. Application Data

(60) Provisional application No. 62/550,825, filed on Aug. 28, 2017.

(51) Int. Cl.
*A61K 9/127* (2006.01)
*A61K 31/355* (2006.01)
*A61K 47/26* (2006.01)
*A61K 31/555* (2006.01)
*A61P 35/00* (2006.01)
*A61K 9/00* (2006.01)

(52) U.S. Cl.
CPC ............ *A61K 9/127* (2013.01); *A61K 9/0019* (2013.01); *A61K 9/1277* (2013.01); *A61K 31/555* (2013.01); *A61K 47/26* (2013.01); *A61P 35/00* (2018.01)

(58) Field of Classification Search
CPC .... A61K 9/127; A61K 9/0019; A61K 31/555; A61K 47/26; A61K 9/1277; A61P 35/00
See application file for complete search history.

(56) References Cited

U.S. PATENT DOCUMENTS

| | | | | |
|---|---|---|---|---|
| 5,186,940 | A * | 2/1993 | Khokhar | A61K 9/127 424/450 |
| 9,090,640 | B2 * | 7/2015 | Bierbach | A61K 45/06 |
| 9,765,103 | B2 * | 9/2017 | Bierbach | C07F 15/0093 |
| 2006/0159739 | A1 * | 7/2006 | Lasic | A61K 9/1271 424/450 |
| 2012/0177726 | A1 * | 7/2012 | Petersen | A61K 33/24 424/450 |
| 2013/0115273 | A1 * | 5/2013 | Yang | A61K 9/1272 424/450 |

OTHER PUBLICATIONS

Trosko, J.E., et al in Mutation Research, 480-481, pp. 219-229, 2001.*

* cited by examiner

*Primary Examiner* — Gollamudi S Kishore
(74) *Attorney, Agent, or Firm* — Fox Rothschild LLP

(57) ABSTRACT

This invention relates to use of a platinum-acridine liposomal formulation and uses thereof in treating cancer in a subject.

23 Claims, 11 Drawing Sheets

Compound P2-A1

Compound P8-A1

Compound P2-A1     Compound P8-A1

FIG. 9A
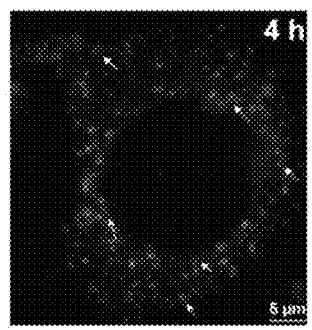
FIG. 9B
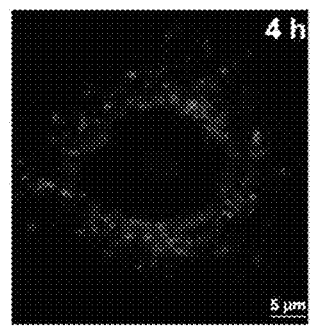
FIG. 10A
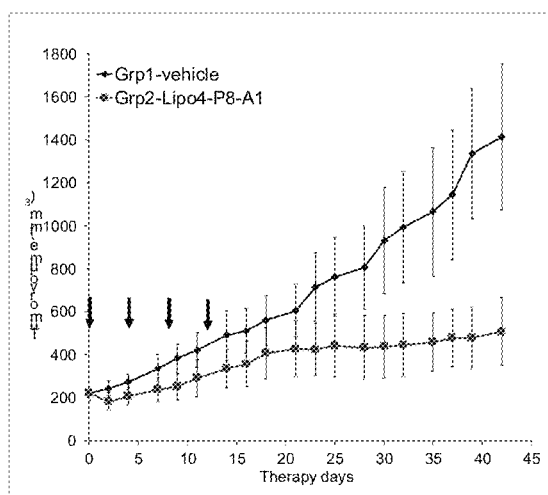
FIG. 10B
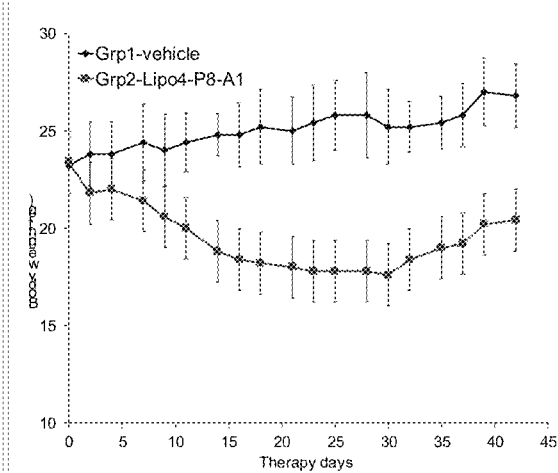
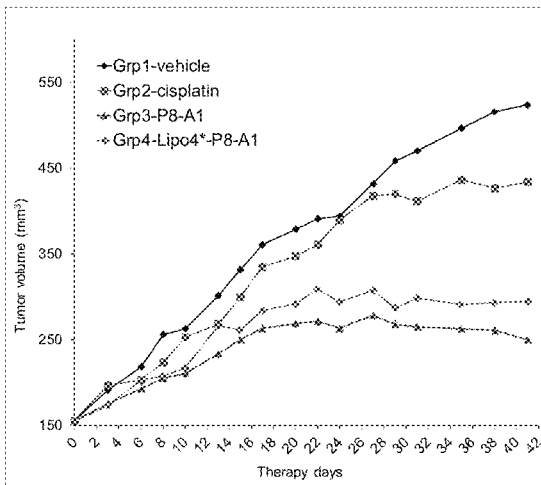
FIG. 10C
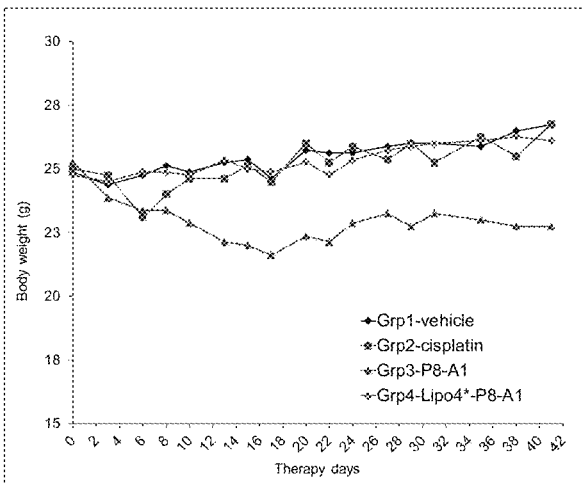
FIG. 10D

LIPOSOMAL FORMULATIONS OF PLATINUM-ACRIDINE ANTICANCER AGENTS AND METHODS THEREOF

CROSS-REFERENCE TO RELATED APPLICATIONS

This application claims priority under 35 U.S.C. § 119(e) to U.S. Provisional Patent Application No. 62/550,825, filed Aug. 28, 2017, which is incorporated herein by reference.

TECHNICAL FIELD OF THE INVENTION

This invention relates to use of a platinum-acridine liposomal formulation and uses thereof in treating cancer in a subject.

BACKGROUND OF THE INVENTION

Platinum-acridine hybrid agents (also referred to as platinum-acridines, or PAs) are 2+ charged, highly hydrophilic molecules, which lead to unfavorable pharmacokinetic (ADME) properties. (Ma, Z., et al. 2008 *Journal of Medicinal Chemistry*, 51, 7574-7580 (1).) Previous studies have suggested that the severe side-effects of PAs in test animals are likely caused by their indiscriminate accumulation in off-target tissues, such as the liver and kidneys. There is a need to improve the toxicity profile of PAs when injected intravenously (i.v.) into subjects.

SUMMARY OF THE INVENTION

This invention addresses the above-mentioned need by providing nanocarrier platforms tailored to the specific chemical and structural requirements of these hybrid PAs to improve their pharmacokinetic properties and overall tolerability for treatment of cancer using PAs.

Stable encapsulation of a dicationic platinum-acridine (PA) cargo in the aqueous core of unilamellar nanoliposomes of well-defined lipid composition, cargo content, size, and physico-chemical properties was achieved using thin-film hydration method, based on a surprising discovery that these liposomes reduce PA accumulation in target organs and toxicity in mice compared to mice treated with PA alone and show efficacy in mouse xenograft model of human cancer. The fusogenic liposomes provide an efficient mechanism of PA cross-membrane transport into cancer cells and promote vesicular transport of PA cargo to the nucleus, the target organelle of PAs.

In one aspect, the present invention provides a PA lipid composition. The composition includes:
(a) a metallopharmaceutical of Formula A:

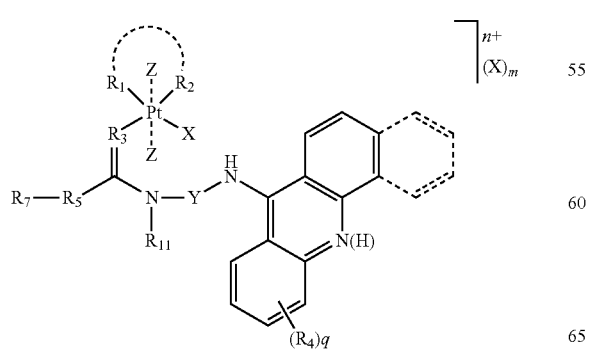

Formula A wherein,
each X is independently halide, —OC(O)R$_9$, nitrate or sulfate;
R$_1$ and R$_2$ are amino groups or together with the platinum atom to which they are attached, R$_1$ and R$_2$ form the ring —NH$_2$—(CH$_2$)$_v$—NH$_2$— wherein v is 1, 2 or 3, or R$_1$ and R$_2$ together can be any of the following groups a-h, or R$_1$ and R$_2$ independently can be any of the following groups i-m;

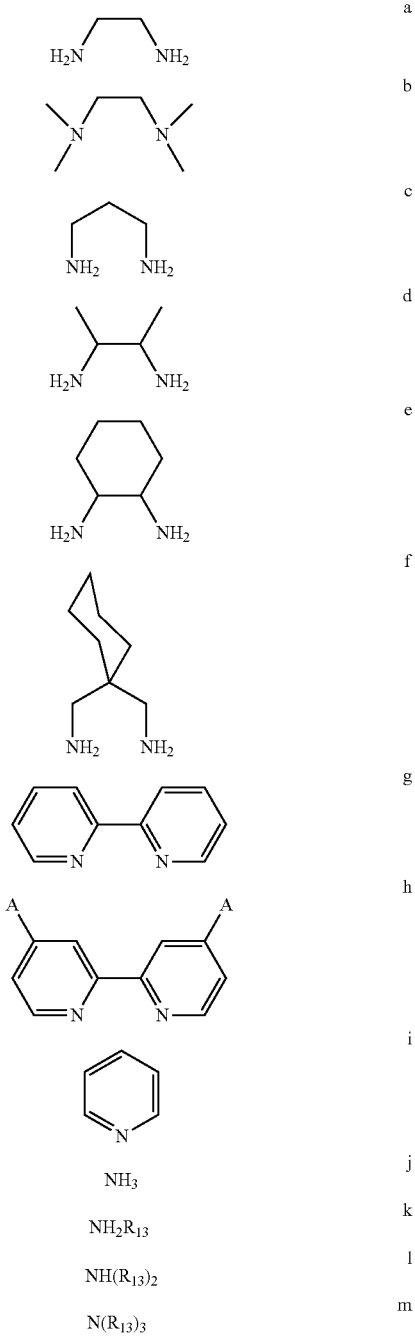

wherein A is H, —CH$_3$, —OCH$_3$, CF$_3$, or NO$_2$;
R$_{13}$ is independently C$_1$-C$_6$alkyl;
R$_3$ is —N(R$_6$)—, wherein R$_6$ is hydrogen or C$_1$-C$_6$alkyl;
R$_4$ is independently an amino, a nitro, —NHC(O)(R$_{10}$), —C(O)NHR$_{10}$, or halo;

$R_{10}$ is hydrogen, $C_{1-6}$ alkyl, phenyl, naphthyl, $C_{3-6}$ cycloalkyl, norhornyl, or adamantyl;

q is 0, 1, or 2;

$R_5$ is a direct bond, —NH— or $C_1$-$C_6$alkylene;

or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, or adamantyl, a natural or unnatural amino acid or a peptide;

$R_9$ is hydrogen, $C_{1-6}$ alkyl, phenyl, naphthyl, $C_{3-6}$cycloalkyl, norbornyl, or adamantyl;

$R_{11}$ is hydrogen or $C_1$-$C_6$alkyl;

n is 1, 2, 3 or 4;

m is 1, 2, 3 or 4;

Y is $C_1$-$C_6$alkylene; and

Z is an additional axial ligand; and (b) an encapsulating lipid mixture, comprising
i. a negatively charged lipid;
ii. a phosphatidylcholine;
iii. a polyethylene glycol-containing lipid;

wherein the negatively charged lipid is more than about 25 mol % in the lipid mixture.

In some embodiments, the metallopharmaceutical molecule ranges from about 1% to about 30% in the composition. In some embodiments, the metallopharmaceutical molecule ranges from about 2% to about 20% in the composition. In some embodiments, the composition is free from cholesterol. In some embodiments, the composition additionally contains cholesterol. In some embodiments, the lipid composition consists substantially of the metallopharmaceutical molecule, a negatively charged lipid, a phosphatidylcholine and a polyethylene glycol-containing lipid. In some embodiments, Z is halide (e.g. Br—, Cl—), OH—, CH3COO—, or RCOO— (R is a substituted or unsubstituted alkyl or aryl). In some embodiments, $(X)_m$ is one or more counterions sufficient to balance the charge of the compound.

In some embodiments, the metallopharmaceutical molecule is

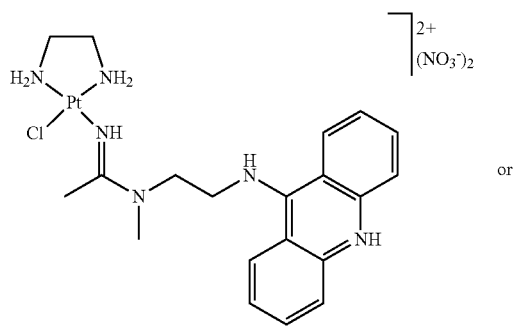

or

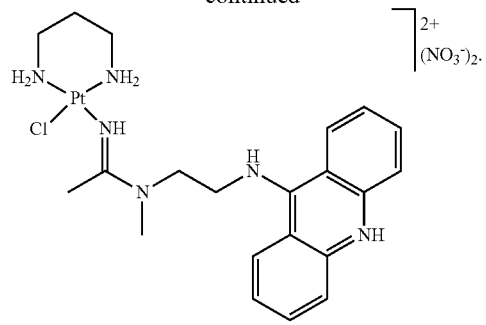

The negatively charged lipid is generally more than about 60 mol % in the lipid mixture. In some embodiments, the negatively charged lipid is 1,2-dihexadecanoyl-sn-glycero-3-phospho-(1'-rac-glycerol) (DPPG).

The phosphatidylcholine ranges from about 5 mol % to about 25 mol % in the mixture. In some embodiments, the phosphatidylcholine is 1,2-Distearoyl-sn-glycero-3-phosphoethanolamine (DSPE).

The polyethylene glycol-containing lipid ranges from about 0.5 mol % to about 15 mol % in the lipid mixture. In some embodiments, the polyethylene glycol-containing lipid is is mPEG-1,2-Distearoyl-sn-glycero-3-phosphoethanolamine (mPEG-DSPE).

In some embodiments, the lipid mixture is a single bilayer of lipids encapsulating the metallopharmaceutical. In some embodiments, the lipid composition has an average diameter of less than about 120 nm.

In another aspect, the present invention provides a method of treating cancer in a subject, comprising administering to the subject a therapeutically effective amount of a PA lipid composition. In some embodiment, the method is applicable to the treatment of solid tumors and can be used in combination regimens. Non-limiting examples of cancers include cancers in lung, colon, breast, pancreatic, skin (melanoma), kidney, and prostate.

In yet another aspect, the present invention provides a method of manufacturing the lipid composition described herein. The method includes:

(a) providing a lipid mixture comprising
i. a negatively charged lipid;
ii. a phosphatidylcholine; and
iii. a polyethylene glycol-containing lipid;
(b) mixing the liquid mixture with a solution comprising the metallopharmaceutical of Formula A to form a liposomal suspension, wherein the ratio by weight between the metallopharmaceutical and the lipid mixture ranges from about 0.01 to about 0.5. In some embodiments, the ratio ranges from about 0.03 to about 0.07.

In some embodiments, step (a) includes adding the lipid mixture to a solvent and removing the solvent to form a film.

In some embodiments, the solution is a 0.9% saline solution. In some embodiments, the solution in step (b) is a saline solution further comprising a cryoprotectant. In some embodiments, the cryoprotectant is selected from the group consisting of mannitol, sucrose, glucose, and glucose. In some embodiments, the cryoprotectant ranges from about 1% to about 15% by weight in the solution.

In some embodiments, step (b) further comprises cooling and heating the liposomal suspension. The cooling and heating (freeze-thaw) process can be repeated multiple times. In some embodiments, step (b) further includes extruding the liposomal suspension through a membrane.

BRIEF DESCRIPTION OF THE DRAWINGS

FIG. 2A illustrates the effect of the freeze-thaw cycles on the encapsulation efficiency (EE %) of DPPG/HSPC/mPEG$_{2000}$-DSPE (80/15/5, molar ratio). The liposomes were prepared using the film-hydration method with an initial drug/lipid ratio of 0.2 (wt/wt). FIG. 2B Effect of the loading buffers on the EE % of DPPG/HSPC/mPEG$_{2000}$-DSPE (80/15/5, molar ratio). The liposomes were prepared using the film-hydration method with 10 freeze-thaw cycles. The initial drug/lipid ratio was set as 0.2 (wt/wt). FIG. 2C Effect of the drug feeds on the EE % of DPPG/HSPC/mPEG$_{2000}$-DSPE (80/15/5, molar ratio). The liposomes were prepared using the film-hydration method with 10 freeze-thaw cycles. FIG. 2D Effect of the lyoprotectants on the EE % of DPPG/HSPC/mPEG$_{2000}$-DSPE (80/15/5, molar ratio). The liposomes were prepared using the film-hydration method with 10 freeze-thaw cycles. The initial drug/lipid ratio was set as 0.2 (wt/wt).

FIG. 4A illustrates TEM image of a single liposome in Lipo-1 highlighting the width of the lipid bilayer. FIG. 4B illustrates TEM image of Lipo-3 which was freshly prepared by cycling ten times through $T_m$. White arrows indicate the formation of bilayer discs. The scale bar indicates 100 nm.

FIGS. 9A and 9B illustrate colocalization images of cells treated with Lipo-1 (FIG. 9 A) and P8-A1 (FIG. 9 B) for 4 h and co-stained with LysoTracker Red. The arrows indicate blue-fluorescent intranuclear vesicular structures that were separated from lysosome. Scale bars represent a distance of 5 µm.

FIGS. 10A, 10B, 10C and 10D illustrate evaluation of P8-A1 and its liposomal formulation, Lipo4-P8-A1, in a A549 xenograft model in mice. FIGS. 10 A-B illustrate tumor volumes and mouse weights monitored for Lipo4-P8-A1 and control, administered q4dx4, i.v. @ 0.4 mg/kg, n=10.

Tumor growth inhibition is 65% on day 41, P<0.05. Mouse weight loss is 22% on day 41, potentially reversible. No other toxicity symptoms noted. FIGS. 10 C-D illustrate tumor volumes and mouse weights monitored for P8-A1 (q4dx4, i.v. @ 0.4 mg/kg), Lipo4*-P8-A1, (q4dx11, i.v. @ 0.4 mg/kg), cisplatin (q4dx11, i.p. @ 4.0 mg/kg), and control (q4dx11, i.v.). A total of 8 mice per group were treated (n=8). See text for discussion. (Note: Lipo4*-P8-A1 is a formulation prepared according to Specific Procedure for Lipo4*-P8-A1, see Experimental Section).

DETAILED DESCRIPTION OF THE INVENTION

The present invention is based on the surprising discovery that nanocarrier platforms tailored to the specific chemical and structural requirements of these hybrid PAs improved their pharmacokinetic properties and overall tolerability for treatment of cancer using PAs.

PAs are 2+ charged, highly hydrophilic molecules, which lead to unfavorable pharmacokinetic (ADME) properties. To improve the toxicity profile of PAs when injected intravenously (i.v.), liposomal encapsulated PAs were prepared, which enhanced permeability and retention (EPR) effect and led to longer circulation times and targeted delivery of PAs to tumor sites. The liposomal PA formulations of the present invention exhibited a higher efficacy when delivered intravenously, with fewer toxic effects observed with the unencapsulated PAs.

Figure 16:
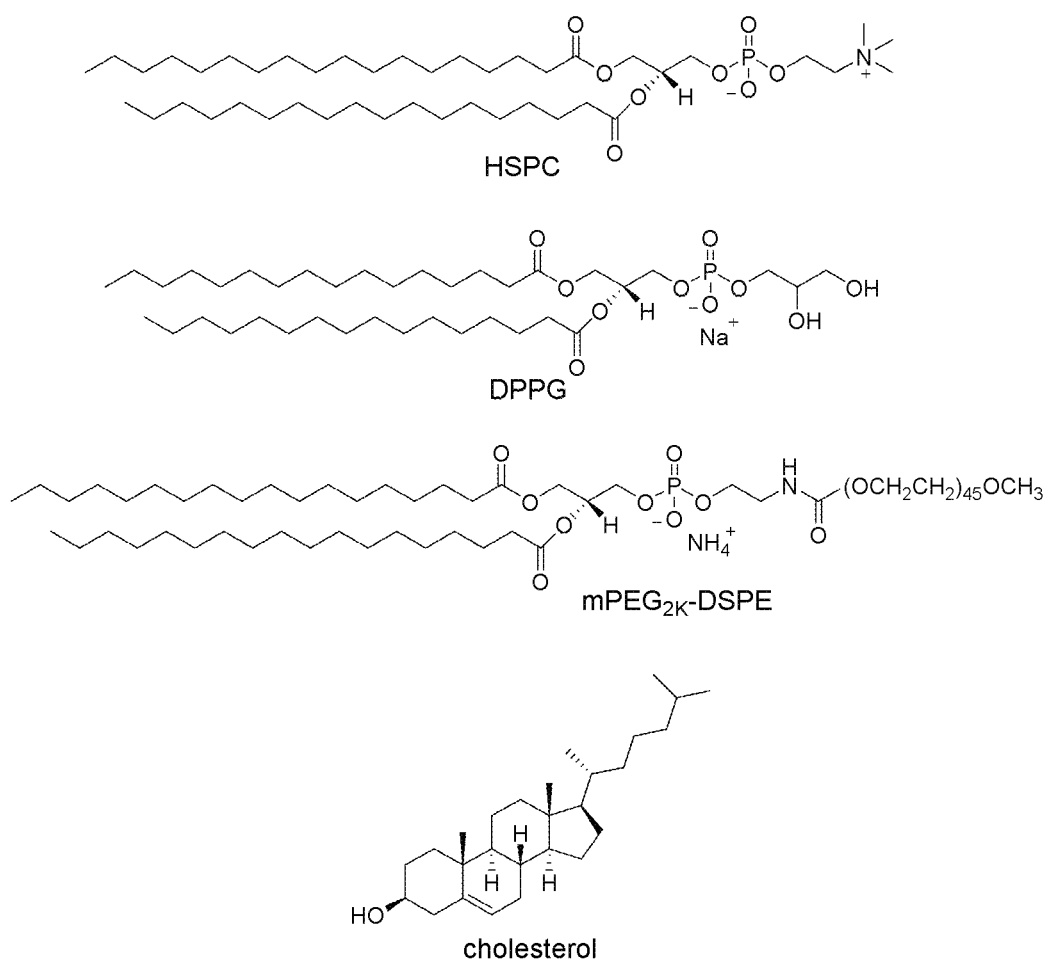
FIG. 16 illustrates examples of chemical structures of lipids used in invention.

Appropriate lipid components with lipids used in FDA-approved Doxil, the liposomal doxorubicin made from hydrogenated soybean phosphatidylcholine (HSPC), cholesterol and polyethylene glycol-2000-distearoylphosphatidylethanolamine (mPEG$_{2000}$-DSPE) were selected (FIG. 16) (3). This combination has been widely used for the encapsulation of other hydrophilic drugs (4). Specifically, HSPC is a lipid with a high phase transition temperature ($T_m$=55° C.), showing an ordered crystalline phase at physiological temperature, which reduces drug leakage during circulation. Incorporation of cholesterol into the lipid bilayer increases the stability of the liposomal formulation (2). Additionally, liposomes decorated with mPEG$_{2000}$-DSPE, a polyethylene glycol-modified lipid, can extend the circulation times of liposome by allowing them to evade the mononuclear phagocyte system (MPS) (2,5). The larger molecular-weight mPEG molecules, however, may slow down cellular uptake and compromise in vivo efficacy (6). Moreover, lipids bearing negative charges, such as 1,2-dihexadecanoyl-sn-glycero-3-phospho-(1'-rac-glycerol) (DPPG), which was chosen in liposomal cisplatin (Lipoplatin) (7), will also be added to the lipid composition. Their electrostatic interactions with the cationic platinum complexes should not only increase the loading capacity, but also enhance drug retention in circulation. Another benefit conferred by DPPG to the liposomes is the ability to fuse with the cell membrane, as demonstrated for lipoplatin (7), which would release the payloads directly into the cytosol of cancer cells.

Definitions

As a person of skill in the art would understand, the present invention encompasses any reasonable combinations of the illustrated embodiments disclosed herein, which would provide a beneficial effect to a cancer patient.

The terminology used in the description of the invention herein is for describing particular embodiments only and is not intended to be limiting of the invention. As used herein, the singular forms "a," "an," and "the" are intended to include the plural forms as well, and vice versa, unless the context clearly indicates otherwise.

The term "about," as used herein, is intended to mean up to ±10% of an indicated value. Any ranges mentioned in the specification or the claims are to be understood as including the range itself and also anything subsumed therein, including both endpoints.

The term "subject," as used herein, generally refers to a mammalian animal, including humans and animals such as dogs, cats, horses, and so on.

The term "composition," "pharmaceutical composition," or "pharmaceutically acceptable composition" means that a composition comprising a PA compound and at least one pharmaceutically acceptable ingredient selected from carriers, diluents, adjuvants, and vehicles, which, as known in the art, generally refer to inert, non-toxic, solid or liquid fillers, diluents, or encapsulating materials unreactive with the PAs.

The liposomal formulations of platinum-acridine anticancer agents, pharmaceutical salts or complexes thereof, can be administered in a variety of ways, for example, orally, subcutaneously or parenterally including intravenous, intraarterial, intramuscular, intraperitoneally, intratonsillar, and intranasal administration as well as intrathecal and infusion techniques. A pharmacological formulation comprising the PAs containing any compatible carrier, such as various vehicles, adjuvants, additives, and diluents can be administered to the patient in an injectable formulation. When administered parenterally, they generally will be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, or the like), suitable mixtures thereof, and vegetable oils. Sterile injectable solutions can be prepared by incorporating the PA formulations in the required amount of the appropriate solvent with one or more of the other ingredients, as desired.

The disclosure is intended to cover any dosage of the PA formulations that can cause therapeutic benefits on a subject having any cancer, although the range of 1 to 200 mg/Kg based on a subject's body weight is disclosed to be generally preferred.

In some embodiments, the method of the present invention may be preferably used in conjunction with other therapies, for example, stem cell transplantation, chemotherapy along with other anticancer drugs, and/or radiation therapy.

EXAMPLES

The following non-limiting examples further illustrate certain aspects of the present invention.

Materials and instruments. All reagents were used as obtained from commercial sources without further purification unless indicated otherwise. HSPC and cholesterol were purchased from Avanti Polar Lipids, Inc. DPPG and mPEG-DSPE were purchased from Lipoid. Polycarbonate membranes with pore size of 100, 200 and 400 nm were purchased from Millipore. Two extrusion devices were used in this study: 1-mL mini extruder (Avanti Polar Lipids, Inc.) and 10-mL LIPEX™ Extruder (Northern Lipids Inc).

Optimization of the encapsulation conditions for P8-A1 using film hydration method. Stock solutions (10 mg/mL) of each lipid were prepared by dissolving in a mixture of chloroform and methanol with the proportion of 3:1 (V/V). To produce the formulations with varying lipid compositions, various combinations of stock solutions, the volumes of which were determined according to the desired molar ratio of lipids, were mixed in a 5-mL round bottom flask to result in solutions containing 10 mg total lipids. The organic solvent was then removed by rotary evaporator and subsequently dried in a oil-pump to allow the formation of a thin lipid film. The lipid film was hydrated at 65° C. in 1 mL of either Milli Q water or 0.9% saline containing 10 mg/mL P8-A1 for 30 min, followed by ten freeze-thaw cycles using liquid nitrogen and a water bath (65° C.). The liposomal suspension was repeatedly extruded at 65° C. through polycarbonate membranes with pore sizes of 200 and 100 nm (10 times each) using a 1-mL mini extruder (Avanti Polar Lipids). The non-encapsulated platinum complex was removed from the liposomal suspension by gel permeation chromatography using a PD-10 Sephadex G-25 column (GE Healthcare, Buckinghamshire, UK), eluted with 0.9% saline solution containing 5% glucose.

Preparation of liposomes using ethanol injection method. The lipids DPPG, HSPC and mPEG-DSPE (80:15:5, molar ratio) were dissolved in 0.4 mL ethanol to produce the alcoholic solution of lipids with a concentration of 25 mg/mL. Next, the ethanol solution was added slowly into 20-times volume of a 0.9% saline solution containing 25 mg/mL P8-A1. The solution was stirred at room temperature for 1 h, followed by dialysis against 0.9% saline solution containing 5% glucose at 4° C. for 24 h. The liposomes formed spontaneously as the ethanol was completely removed after dialysis. The liposomal suspension in water was then filtered through the 220 nm filter membrane for sterilization, and stored at 4° C.

Preparation of liposomes using reverse phase evaporation method. DPPG, HSPC and mPEG$_{2000}$-DSPE at a molar ratio of 80:15:5 (the total weight of lipids is 10 mg) were dissolved in a mixture of chloroform and diethyl ether (1:2, v/v), which was added into an aqueous solution containing 2 mg of P8-A1 dissolved in 0.9% saline/5% glucose solution. The ratio of aqueous to organic phase was 1:3 (V/V). The mixture was then sonicated at room temperature for 10 min, and the organic solvents were slowly removed by rotary evaporation. The resultant aqueous suspension was extruded with a mini extruder following the method described in section 7.4.2.

Scaled-up preparation of liposomal formulations for biological evaluation. General procedure. Liposomes used for biological testing were prepared using the film hydration method as described in the discussion. The formulations were homogenized using a 10-mL LIPEX™ Extruder (Northern Lipids Inc.). The unbound platinum complex was removed from liposomal suspension by gel permeation chromatography using a PD-10 Sephadex G-25 column (GE Healthcare, Buckinghamshire, UK), eluted with 0.9% saline/5% glucose solution, followed by dialysis against 0.9% saline/5% glucose solution at 4° C. for 24 h. The liposomal formulations were stored at 4° C.

Detailed procedure for Lipo4*-P8-A1. Because this low-payload formulation is generated at a low drug feed, the procedure requires a relatively high concentration of lipid to achieve the desired final concentration of P8-A1, resulting in highly viscous solutions incompatible with the extruder design. Thus, the mixtures had to be extruded in smaller, more dilute batches than those prepared for the higher drug:lipid ratios. In addition to gel filtration, exhaustive dialysis and centrifugal filtration had to be performed to completely remove unencapsulated P8-A1 from the liposomes and to concentrate the samples to a level suitable for in vivo testing, respectively. Likewise, it was necessary to reduce the lipid concentration loaded onto the size-exclusion columns (SG-25) to achieve efficient separation of formulation and unencapsulated P8-A1 (as observed for high payloads, see Lipo1 in FIG. 5). Lipo4*-P8-A1 was prepared with a lipid mixture containing DPPG, HSPC, and mPEG-DSPE (20:75:5), which underwent hydration after generating a thin film from organic solvent (volume ratio, chloroform:methanol=3:1). Specifically, 17.0 mg of DPPG, 67.1 mg of HSPC, and 15.9 mg of mPEG-DSPE based on that aforementioned molar ratio (100 mg lipid) were dissolved in this solvent mixture. After removing all solvent by rotary evaporation, the film was dried in an oil pump vacuum at room temperature for 12 h. The solution of P8-A1 was prepared in 0.9% saline containing 5% glucose as the loading solution. The initial drug feed was 0.1% based on drug:lipid weight ratios (mg drug:mg lipid). Specifically, 10 mg of P8-A1 was dissolved in 4 mL of 0.9% saline containing 5% glucose. The dry film was hydrated with drug solution at 60° C. followed by 10 freeze-thaw cycles (five minutes freeze, five minutes thaw), using liquid nitrogen (−196° C.) and hot water, which was maintained above 60° C. During each thaw cycle, heating was continued in a sonicated water bath maintained at 60° C. for another 2.5 min, followed by polycarbonate membrane extrusion with membrane pore sizes of 0.4 um, 0.2 um, and 0.1 um (10× each). The extruder was cleaned with methanol to remove any previous debris 6 h before extrusion was taking place. It was then flushed with 0.9% saline containing 5% glucose five times right before use and maintained at a temperature between 60° C. and 70° C. Individual batches of Lipo4*-P8-A1 were combined, and the final extrusion step (0.1 um) was repeated to assure sample homogeneity. The extruded liposomes were then purified on Sephadex G-25 columns (GE Healthcare) using 0.9% saline solution as the eluent and subsequent dialysis for 24 h against a 0.9% saline. Finally, the solution was concentrated in 15-mL Amicon centrifugal filter devices (30,000 MW) at 5,000 rev/min to the desired drug concentration required for in vivo testing. A combined batch of this formulation, equivalent to 3.44 mg of P8-A1, was generated in this manner (lipid:drug ratio, 2.05%; DLS size, 107.7±0.3 nm; PDI, 0.042±0.006; zeta-potential, −34.5±0.6 mV; see Figure Ax for DLS results on a sample from the combined batches of Lipo4*-P8-A1).

Size and zeta potential of liposomes. Liposome suspensions (~10 mg/mL lipids, 25 µL) were diluted in 1 mL of Milli-Q water and filtered through a membrane filter with a pore size of 220 nm. The hydrodynamic diameter was assessed by dynamic light scattering (DLS) using a Zetasizer ZS90 (Malvern Instruments) in automatic mode (Software version 6.34) using the instrument's default settings for refractive index and viscosity of the dispersant. All measurements were run at 25° C. The zeta-potential of was assessed in Milli-Q water at pH 6.8-7 using the Zetasizer ZS90 instrument. Triplicate measurements were performed. The results are presented as particle sizes and charges±SD.

Transmission Electron Microscopy. The liposome samples were diluted before analysis with 0.9% saline and then pipetted on carbon-stabilized Formvar copper grids. Excess sample was removed with a filter paper. A drop of 2% (w/v) aqueous solution of uranyl acetate was added and the sample was allowed to stain for 1 min. The samples were dried at room temperature and then imaged using FEI Tecnai BioTwin Transmission Electron Microscope operated at 80 kV. The images were captured with an AMT 2vu camera capable of 12 megapixel images and analyzed with the included AMT camera software.

Encapsulation efficiency of liposomes. To determine the content of P8-A1 entrapped in the liposomes, methanol was used to lyse the liposomal lipid bilayer. Briefly, 100 µL of liposomes before and after purification were mixed with 1900 µL of methanol. The mixtures were sonicated for 15 min and the amount of platinum-acridine was determined spectrophotometrically at 413 nm ($\varepsilon_{413}$=10000 $M^{-1}$ $cm^{-1}$). Encapsulation efficiencies (EE %) were determined using the following equation: EE %=($[Drug]_{purified}$/$[Drug]_{initial}$)×100%.

Determination of lipid composition. Phospholipids concentration was determined using Bartlett's assay (19). The assay relies on the interaction between the inorganic phosphates and ammonium molybdate, which can be monitored by reaction with 4-amino-3-hydroxyl-1-naphtalene sulfonic acid at 180° C. to yield a blue-colored product and quantified at 815 nm. The amount of cholesterol was quantification by reversed phase HPLC using a UV detector with the wavelength at 207 nm. The samples were separated using a 4.6 mm×150 mm reverse-phase Agilent ZORBAX SB-C18 (5 mm) analytical column at 25° C., by using the following solvent system: solvent A, optima water, and solvent B, methanol/0.1% formic acid, with a flow rate of 0.5 mL/min and a gradient of 95% A to 5% A over 20 minutes.

Drug leakage under physiologically relevant conditions. Liposomal formulations (~1 mg/ml lipids) were incubated in 1 Ml PBS (pH 7.4) at 37° C. At selected time-points, samples (in triplicate) were eluted with 0.9% NaCl solution by size exclusion chromatography using PD-10 Sephadex G-25 columns to remove released free P8-A1. The amount of drug retained was then measured spectrophotometrically.

In vitro drug release of P8-A1 at elevated temperature. Lipo-1 (~1 mg/mL lipids) was incubated in 1 mL PBS (pH 7.4) at 42° C. and 44° C. At selected time-points, samples (in triplicate) were eluted with 0.9% NaCl solution by size exclusion chromatography using PD-10 Sephadex G-25 columns to remove released free P8-A1. The amount of drug retention was then measured spectrophotometrically.

Storage stability. Purified liposomal formulations (10 mL) were sterilized by passing them through 0.22 µm membrane filters and stored at 4° C. for 1, 4, and 8 weeks. Samples were tested for particle size and drug retention within liposomes. The particle size was evaluated by DLS measurements. To determine the concentration of encapsulated P8-A1, samples were passed through PD-10 Sephadex G-25 columns and eluted with 0.9% saline solution to remove any free platinum complex. The amount of drug retented was then measured spectroscopically as described above. The samples before the storage were used as controls. The liposomes lysed by methanol were used as positive controls. Measurements were performed in triplicate.

Cellular uptake of Lipo-1 in NCI-H460. NCI-H460 cells were seeded into poly-d-lysine coated glass-bottom Petri dishes (MatTeck Corporation, Ashland, Md., USA) with $10^5$ cells $mL^{-1}$ suspended in 2 mL of medium per dish. Cells were incubated overnight and then treated with Lipo-1 and P8-A1 (5 µM), or medium for controls for designed time points. After treatment, medium was removed and the cells were stained with 75 nM of LysoTracker Red DND-99 (Invitrogen) in 2 mL pre-warmed Hank's Balanced Salt Solution (HBSS) at 37° C. for 30 min. After staining with LysoTracker, solutions were replaced with fresh medium. Images were collected using a Zeiss LSM 710 confocal microscope (Carl Zeiss MicroImaging, Thornwood, N.Y.) using a 63× (PLAN APO, 1.2 NA) objective lens. All images were acquired in multi-track configuration mode to minimize excitation cross talk and emission bleed-through. The fluorescence of P8-A1 (blue), and Lyso-Tracker Red DND-99, was excited/collected at 405/477 nm and 561/591 nm, respectively. ZEN software (blue edition, Carl Zeiss, 2011) was used for image processing. Confocal image planes for each channel were not contrast-adjusted (unless indicated) or otherwise changed. Panels were assembled and annotated without any additional manipulation of images in Adobe Photoshop CS2.

Evaluation of maximum tolerated dose (MTD). MTD of P8-A1 and liposomal formulations were evaluated in Swiss-Webster female mice (5 to 6 week-old, 22-25 g). Mice (5 per group) were treated i.v. with the doses ranging from 0.2-0.8 mg/kg every four days for four times. The acute toxicity was assessed based on animal survival and visual signs of toxicity including body weight loss (BWL) and clinical signs. Clinical signs observed were piloerection or hunched posture. Animals displaying mild piloerection were considered to be indicating mild toxicity at that dose.

A549 Xenograft study. A549 xenografts were established in nude athymic female mice via subcutaneous injections. Treatment began when the average tumor volume was approximately 100-200 $mm^3$. The tumor-bearing mice were randomized depending on tumor volume into groups of 8 or 10 test animals each. Animal weights and tumor volumes were measured and recorded throughout the entire study after the first dose was administered. Tumor volumes were determined using the formula: V $(mm^3)=d^2 \times D/2$, where d and D are the shortest and longest dimension of the tumor, respectively, and are reported as the sum of both tumors for each test animal. At the end of the study, all animals were euthanized and disposed off according to Standard Operating Procedures (SOPs). One tumor per test animal as well as lungs, spleens, and kidneys were removed during necropsy. The concentration of Pt in selected tissues was determined by quadrupole inductively-coupled mass spectrometry (ICP-MS) on a Thermo ICP-MS instrument at the Analytic Chemistry Service facility of Research Triangle Institute, Research Triangle Park, N.C. The xenograft study was performed by Washington Biotechnology Inc. (Simpsonville, Md.), PHS-approved Animal Welfare Assurance, #A4912-01. Data analysis for weight and tumor volumes was done with the Student's t-test. Only P values of less than 0.05% were considered as statistically significant.

Example 1

Aqueous Stability of Platinum-Acridine Analogues

Figure 1:
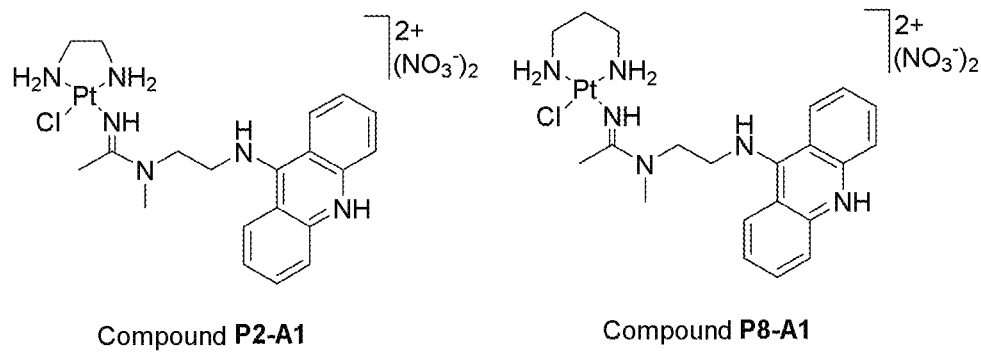
FIG. 1 illustrates chemical structures of PA derivatives introduced as cytotoxic cargoes.

Prior to liposomal encapsulation of PAs, P2-A1 (FIG. 1) was selected as a representative PA derivative for aqueous stability studies in water and 0.9% saline at 60° C., the temperature above the transition temperature that was required for the preparation of the liposomes. All samples were incubated for 4 hours, which is significantly longer than the time required for encapsulation, and the reaction mixtures were characterized by liquid chromatography-mass spectrometry (LC-MS). P2-A1 was found to be sufficiently stable in saline, but underwent aquation in Milli Q water under the test conditions. Aquation typically occurs when the environmental chloride level is low and can be suppressed by a high level chloride ions in solution at 37° C. (for example, 150 mM NaCl) (8). This experiment indicated that 0.9% saline can completely inhibit this ligand exchange reaction at high temperature (60° C.) for at least 4 h. To avoid loss of chloro ligand in P2-A1 during the loading procedure and further decomposition of the hybrid agent, 0.9% saline in water was used as the loading media for the preparation of all liposome samples.

Optimization of Conditions for Drug Loading

Selection of Lipids

The optimal lipid composition for the encapsulation of P8-A1 (FIG. 1), the most cytotoxic platinum-acridine analogue identified to date was screened (9). A library of liposomes (Table 1) with various combination of lipid components was prepared on a small scale (10 mg of total lipids for each) with a 1-mL mini-extruder using the film-hydration method. In the screen, all the preparations were performed in Milli Q water with the same initial drug feeds, defined as the relative ratio of "mg of Pt complex/mg of total lipids". The content of mPEG was fixed at 5 mol % in the library, which is based on the calculation for the estimated surface coverage of mPEG-DSPE$_{2000}$ for 100-nm sized liposomes (10). Higher degrees of PEGylation will not have a significant impact on the stabilities in circulation, but may introduce multiple populations of nanoparticles, including mixed micelles and discs, if the content of mPEG is higher than 15 mol % (10,11). The liposomal encapsulations were evaluated based on their encapsulation efficiency (EE %, Table 1). In initial experiments liposomes containing HSPC and cholesterol, such as liposomes 1-3 (Lipo-1-Lipo-4) (Table 1) were used. No encapsulation of P8-A1 was observed for these formulations, which can be attributed to the poor lipid affinity of the cationic platinum complex. The addition of 30 mol % DPPG, as expected, greatly increases EE % to 32±1%, as evidenced in liposome 4 (Lipo-4) compared with all the DPPG-free liposomes. This improvement can be explained with the electrostatic interaction of DPPG with the cationic payload, which facilitates drug uptake into the aqueous core. The encapsulation efficiency increases as more DPPG is incorporated into the lipid bilayer, with the EE % reaching 53±2% for a DPPG content of 45 mol %.

No adverse consequences for the drug loading were observed when the content of HSPC and cholesterol was varied (Table 1). However, the inclusion of these components is essential for maintaining the in vivo stability of the liposomes. For example, addition of cholesterol enhances the retention of payloads in the liposomes that are mainly composed of lipids with a phase transition temperature ($T_m$) lower than 37° C. They increase the permeability of the gel phase bilayers ($T_m$>37° C.) under physiological conditions. In the latter case, incorporation of cholesterol may impede drug release (12), leading to a reduction in anticancer efficacy. Therefore, two cholesterol free liposomes were also included in the library. In particular, 87% of P8-A1, the highly hydrophilic molecule, was successfully encapsulated in formulation 9 made of DPPG, HSPC and mPEG-DSPE (80:15:5, molar ratio). High blood stability of cholesterol-free liposomes comparable to conventional cholesterol-containing liposomes has been demonstrated when phospholipids with a high $T_m$, such as DPPC, DPPG and HSPC, are major components of the bilayers (13). Decoration of cholesterol free liposomes with mPEG further improves their in vivo stability and prolongs their circulation time in blood (2).

TABLE 1

Conditions for Liposomal Encapsulation of P8-A1

| # | Lipid Components | Lipids Ratio (molar) | Initial Drug/Lipid (wt) | Loading media | EE % |
|---|---|---|---|---|---|
| 1 | HSPC/CHOL/mPEG-DSPE | 55/40/5 | 0.2 | H$_2$O | 0 |
| 2 | HSPC/CHOL/mPEG-DSPE | 73/24/5 | 0.2 | H$_2$O | 0 |
| 3 | HSPC/mPEG-DSPE | 95/5 | 0.2 | H$_2$O | 0 |
| 4 | DPPG/HSPC/CHOL/mPEG-DSPE | 30/25/40/5 | 0.2 | H$_2$O | 32 ± 1% |
| 5 | DPPG/HSPC/CHOL/mPEG-DSPE | 45/15/40/5 | 0.2 | H$_2$O | 53 ± 2% |
| 6 | DPPG/HSPC/mPEG-DSPE | 50/45/5 | 0.2 | H$_2$O | 36 ± 2% |
| 7 | DPPG/HSPC/mPEG-DSPE | 80/15/5 | 0.2 | H$_2$O | 87 ± 2% |
| 8 | DPPG/HSPC/mPEG-DSPE | 80/15/5 | 0.5 | H$_2$O | 45 ± 2% |
| 9 | DPPG/HSPC/mPEG-DSPE | 71/24/5 | 0.2 | H$_2$O | 46 ± 1% |
| 10 | DPPG/HSPC/mPEG-DSPE | 47.5/47.5/5 | 0.2 | H$_2$O | 39 ± 1% |
| 11 | DPPG/HSPC/mPEG-DSPE | 80/15/5 | 0.2 | 0.9% Saline | 49 ± 1% |
| 12 | DPPG/HSPC/mPEG-DSPE | 80/15/5 | 0.2 | 0.9% Saline | 30 ± 0.3% |
| 13 | DPPG/HSPC/mPEG-DSPE | 80/15/5 | 0.2 | 5% Sucrose, 0.9% Saline | 72 ± 1% |
| 14 | DPPG/HSPC/mPEG-DSPE | 80/15/5 | 0.2 | 5% Sucrose, 0.9% Saline | 40 ± 2% |

The Importance of Freeze-Thaw Cycles for Drug Loading

Figure 2A:
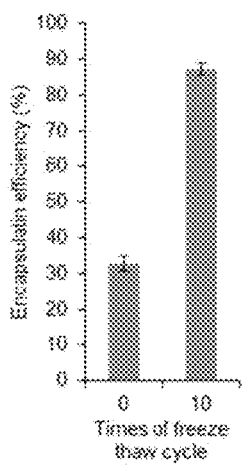
FIGS. 2A, 2B, 2C and 2D.
Figure 2B:
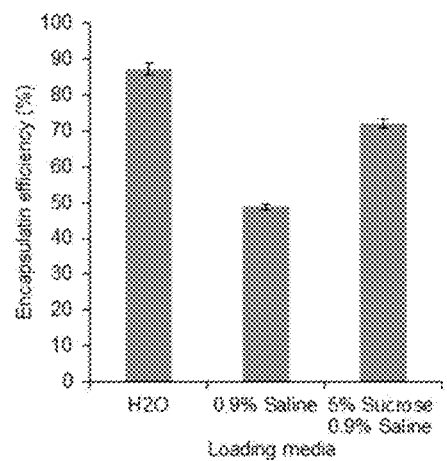

A library of liposomal formulations was prepared using 10 freeze-thaw cycles during which the liposomal suspensions were frozen in liquid nitrogen (−196° C.), thawed, and heated at a temperature above the Tm of the bulk lipids. To evaluate the impact of freeze-thaw cycles on the encapsulation of P8-A1, a cholesterol-free liposome formulation without undergoing freeze-thaw process has also been generated with the bilayer compositions identical to liposome 9 in the library. Results are shown in FIG. 2A. Strikingly, about 54% more drug was encapsulated when applying the freeze-thaw technique, confirming its importance in the drug loading process. The freeze-thaw technique has been widely implemented to improve the encapsulation of hydrophilic drugs. It has been proposed that the process causes a re-equilibration of drug distribution inside and outside the liposomes, most likely due to disruption of the lipid bilayers caused by the formation of ice crystals (14,15). An increase in the trapping volume was also observed after freeze-thaw cycle, which improves the encapsulation yield (15). Moreover, since the liposomes lacking cholesterol are very sensitive to changes in temperature and osmotic gradients, the freeze-thaw technique is likely to be more effective for the cholesterol free liposomes than conventional formulations (16).

Influence of Loading Buffers on Drug Loading

The roles of the loading buffers were assessed in the liposomal encapsulation process. Milli Q water, 0.9% saline, and 0.9% saline containing various cryoprotectants (glucose, sucrose and mannitol) were used in this study to hydrate the lipid thin film composed of DPPG, HSPC and mPEG-DSPE (80:15:5, molar ratio). The drug feeds were set as 0.2. The EE %, obtained after 10 freeze-thaw cycles, is shown in the FIG. 2D. The use of water yielded a formulation with EE % of 88%, which dropped notably to about 49% when the loading solution was replaced with 0.9% saline. This can be in part explained by the increased ionic strength of the loading solution, which weakens the electrostatic interactions of the lipid bilayer with the cationic platinum compounds, and therefore reduces the amount of encapsulated drug. In addition, the high concentration of NaCl (~150 mM) in saline inhibited the phase separation of ice and solute during freezing and thus strongly inhibited liposomal encapsulation (17). The addition of cryoprotectants can partly restore the EE %. Specifically, 72% of P8-A1 was encapsulated using 0.9% saline containing 5% glucose as the loading solution. The cryoprotectants form multiple hydrogen bonds with the lipids. This interaction stabilizes the bilayers, preventing them from being completely disrupted during freeze-thaw cycles, which leads to the leakage of loaded drug. The increase in the amount of glucose from 5% to 10% did not result in significant changes in EE. Since P8-A1 may undergo aquation in water at high temperature, we decided to use 0.9% saline containing 5% as the loading solution to suppress this process.

Influence of Drug Feeds on Drug Loading

Figure 2C:
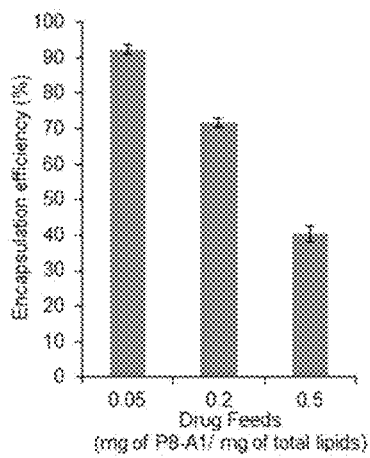
Figure 2D:
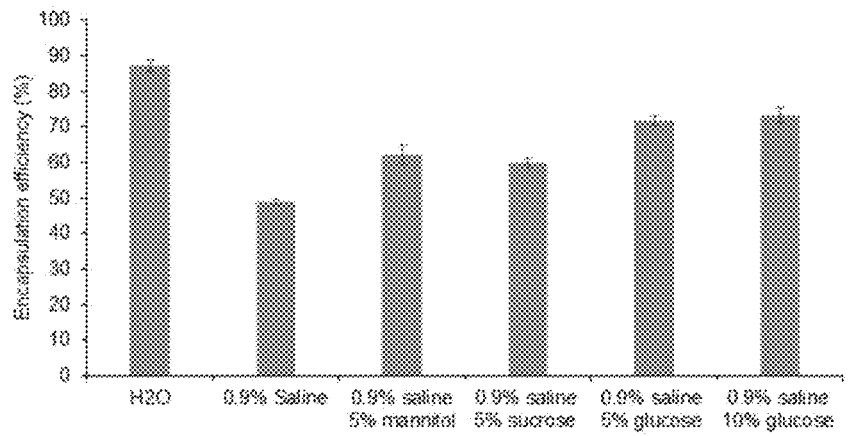
Figure 3A:
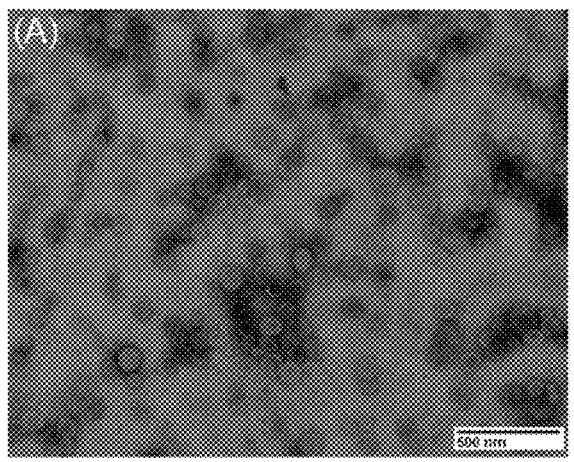
FIGS. 3A, 3B, 3C and 3D illustrate TEM images of Lipo-1 (FIG. 3 A), Lipo-2 (FIG. 3 B), Lipo-3 (FIG. 3 C) and Lipo-4 FIG. 3 (D). Liposomes were negatively stained using uranyl acetate.
Figure 3B:
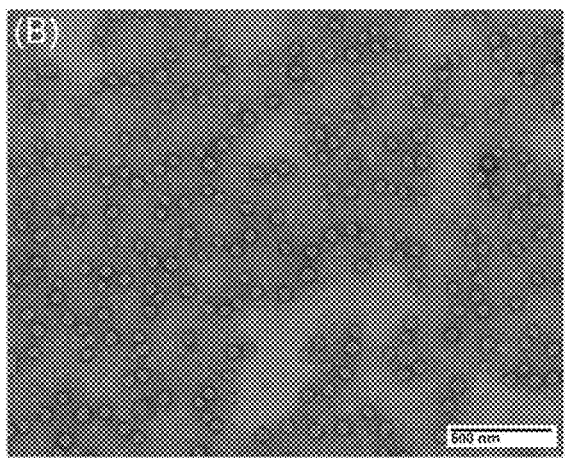
Figure 3C:
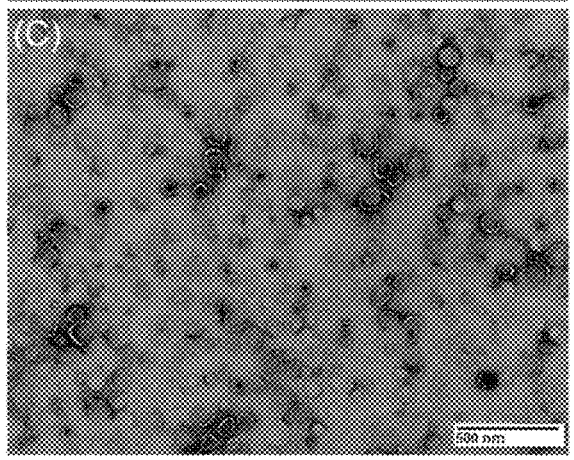
Figure 3D:
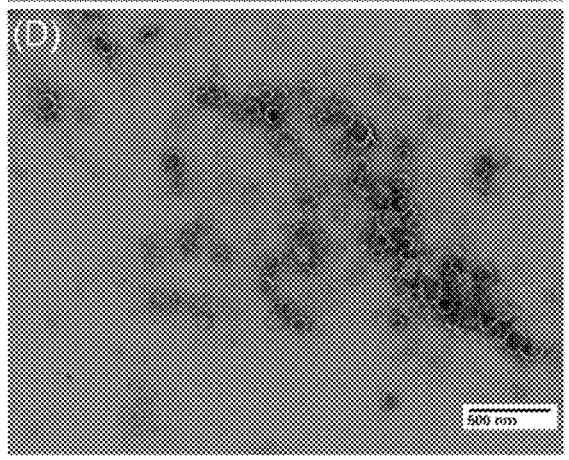

To evaluate the effects of initial amounts of drug on encapsulation, drug feeds of 0.05, 0.1 and 0.2 were chosen in this study (FIG. 2C). A formulation with the EE % of 92% was produced with a drug feed of 0.05, which dropped to 72% as the drug feed was increased to 0.2. This occurs because with lower drug feed (higher DPPG:P8-A1 ratio), negatively charged lipids in the core can better wrap up the cationic platinum complexes, which leads to higher EE %. In addition, about 60% of P8-A1 was not encapsulated in the liposomes when the drug feed was increased to 0.5. This is caused by amount of dicationic P8-A1, which electrostatically neutralize the negatively charged DPPG and lead to saturation with payload. Drug feeds higher than 0.5 were found to result in the formation of yellow precipitate regardless of the drug concentration, possibly due to complete neutralization of lipids with platinum complexes.

Influence of Loading Methods on Drug Loading

Different methods of formulating liposomes for P8-A1 were compared, including film hydration, reverse-phase evaporation, and ethanol injection (18). All the formulations in this study were prepared with the lipid component DPPG, HSPC, and mPEG-DSPE (molar ratio: 80:15:5) using 0.9% saline containing 5% sucrose as the loading buffer, with an initial drug feed of 0.2. The film hydration method resulted in the formulation with the highest EE % of about 80%, while a significant drop in EE % was observed in the formulations prepared by reverse-phase evaporation (21%).

This method commonly leads to higher EE % than others for encapsulation of hydrophilic drugs because a large internal aqueous volume is generated in the preparation. This observation confirms our previous finding that the freeze-thaw procedure is critical for achieving the highest EE %. Less than 5% of P8-A1 was entrapped in the liposomes using ethanol injection under the same conditions. Because drug loading with this technique relied on the self-assembly of the lipids with platinum complexes, poor partitioning of P8-A1 between lipids and aqueous solution may be responsible for the lower EE %. In addition to EE %, the hydrodynamic size of these liposomes generated by different methods were examined using dynamic light scattering (DLS) measurements. Liposomes prepared by film hydration and reverse-phase evaporation method, which underwent serial extrusion through 0.22 µM membranes, were homogeneous with a diameter of approximately 120 nm (polydispersity index, PDI<0.2), whereas the ethanol injection method without extrusion generated 133 nm liposomes with a broad size distribution (PDI>0.2). As a result, film hydration and subsequent extrusion is a better method for encapsulating PAs and was chosen for all formulations prepared for further biological evaluation.

Example 2

Characterization of Liposomes

Four PEGylated liposomal formulations of P8-A1, denoted as Lipo-1-4, were prepared for the following biological evaluations (compositions and properties are summarized in Table 2). Lipo-1, which had the highest loading capacity, was a cholesterol-free liposomal formulation with the lipid composition of DPPG, HSPC, and mPEG-DSPE at a molar ratio of 80:15:5. Lipo-2 was inspired by lipoplatin (7), liposomal cisplatin, which is currently in phase II/III clinical trials and is composed of DPPG, HSPC, cholesterol, and mPEG-DSPE. Lipo-3 is composed of the identical lipid components as Lipo-1 but with lower drug loading capacity. Lipo-4, containing the same lipids as Lipo-1 yet with reduced level of DPPG in the bilayers, was produced to evaluate the role of DPPG in the formulation. The average hydrodynamic diameter of all the formulations, determined by dynamic light scattering (DLS), were approximately 110-120 nm with small polydispersity indices (PDI) of less than 0.2, suggesting highly homogeneous size distributions (FIGS. 11-15). The liposomes with a size of about 100 nm are optimal for in vivo applications since they show favorable tumor retention and long circulation time in blood (2).

It was determined that liposome size correlates with drug loading capacity, with larger diameters in the formulations producing higher drug-to-lipid ratios. In addition, due to the presence of anionic DPPG, all formulations showed negative zeta potentials. This also confirms that the cationic platinum complexes did not localize to the liposome surface, but remained trapped within the aqueous core. Reduction of the zeta potential from ~−40 mV in Lipo-1 to −29 mV in Lipo-4 was found as the amount of DPPG decreased. Less negatively charged liposomes are thought to have a longer circulating time, which may result in an enhanced EPR effect (2). The relative amounts of phospholipids and cholesterol were determined with Bartlett assay (19) and reverse-phase HPLC, respectively. Lipo-1 containing a high level of DPPG was found to be able to reach a drug-to-lipid ratio of 19.7% (wt/wt), while the drug-to-lipid ratio of Lipo-2, which contained less DPPG and 9.3% (wt/wt) cholesterol, was 6.8% (wt/wt). This value considerably dropped to 2.3% (wt/wt) in formulation Lipo-4, which contained the lowest concentration of DPPG. Thus, the content of DPPG dominates the encapsulation efficiency of P8-A1.

Figure 4A:
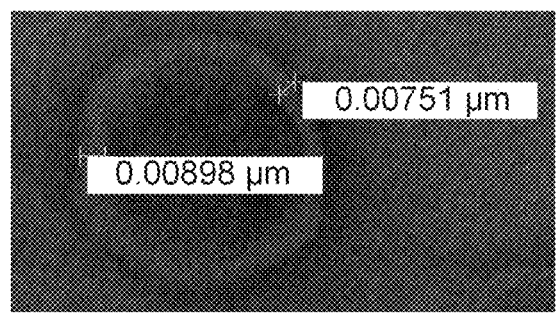
FIGS. 4A and 4B.
Figure 4B:
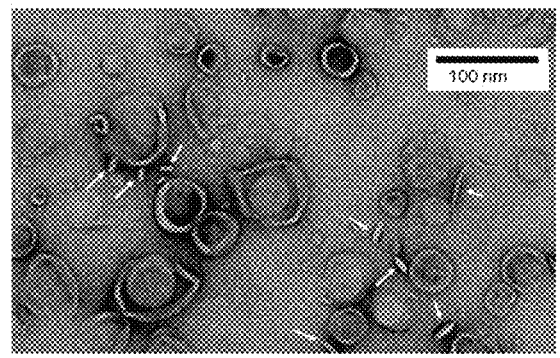

To further characterize the liposomes, transmission electronic microscopy (TEM) was exploited to reveal structural details. All liposomes were negatively stained with uranyl acetate prior to TEM image acquisition. Most of the liposomes were found to be spherical with a size of less than 100 nm, which was smaller than the results obtained with DLS. This difference in apparent size is typically observed in PEGylated liposomes, in which the hydrophilic PEG residues form a hydration layer on the surface in solution. This makes the particle size appear large when measured by DLS (2). TEM also showed an electron-dense platinum-filled core wrapped in a brighter layer in the cholesterol-free formulations Lipo-1, Lipo-3, and Lipo-4. Measurement of the thickness of the liposomal bilayer exhibited a range from 6 to 9 nm (FIG. 4A). Because the thickness of a double lipid bilayer should be at least 10.4 nm (17), these liposomes consisted of a single bilayer of lipids.

Figure 17:
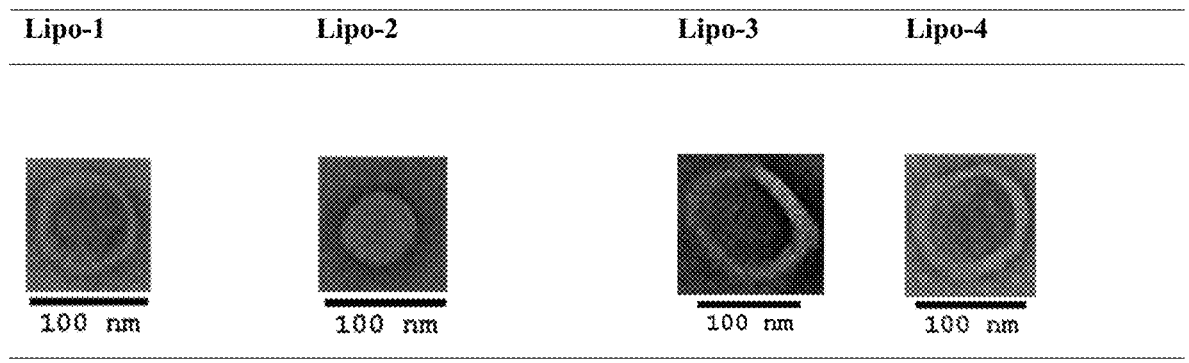
FIG. 17 illustrates TEM images of four liposomal formulations prepared for P8-A1.

By contrast, no fine structure was observed in Lipo-2. Ruptured liposomes and disc-like structures (FIG. 5B) were found in Lipo-3 and Lipo-4. This typically occurred in the cholesterol-free liposomes containing DSPE-mPEG after undergoing freeze-thaw cycles throughout their $T_m$ (20). This effect was not observed in Lipo-1, the cholesterol free formulation with the highest loading capacity, suggesting that PAs may help stabilize the lipid bilayer during the freeze-thaw process. FIG. 17 shows TEM images of four liposomal formulations prepared for P8-A1.

TABLE 2

Characterization of Four Liposomal Formulations Prepared for P8-A1

|  | Lipo-1 | Lipo-2 | Lipo-3 | Lipo-4 |
|---|---|---|---|---|
| Lipid components | DPPG:HSPC:DSPE-mPEG$_{2k}$ (molar ratio: 80:15:5) | DPPG:HSPC:Chol:DSPE-mPEG$_{2k}$ (molar ratio: 40:32:20:8) | DPPG:HSPC:DSPE-mPEG$_{2k}$ (molar ratio: 80:15:5) | DPPG:HSPC:DSPE-mPEG$_{2k}$ (molar ratio: 20:75:5) |
| Payload$^a$/lipid$^b$ (wt/wt), (reported as % payload) | 19.7 ± 1.7 | 6.8 ± 0.4 | 1.7 ± 0.2 | 2.3 ± 0.3 |
| Cholesterol (wt %)$^c$ | — | 9.3 ± 0.6 | — | — |
| Size (nm)$^d$ | 120.9 ± 1.1 | 112.3 ± 1.6 | 110.7 ± 1.2 | 102.4 ± 0.7 |
| PDI$^d$ | 0.073 ± 0.009 | 0.037 ± 0.015 | 0.127 ± 0.027 | 0.122 ± 0.009 |
| Zeta potential (mV)$^d$ | −47.4 ± 0.8 | −41.7 ± 1.0 | −40.7 ± 0.7 | −29.2 ± 0.1 |

Example 3

Stability of Liposomes in PBS and During Long-Term Storage

Figure 5:
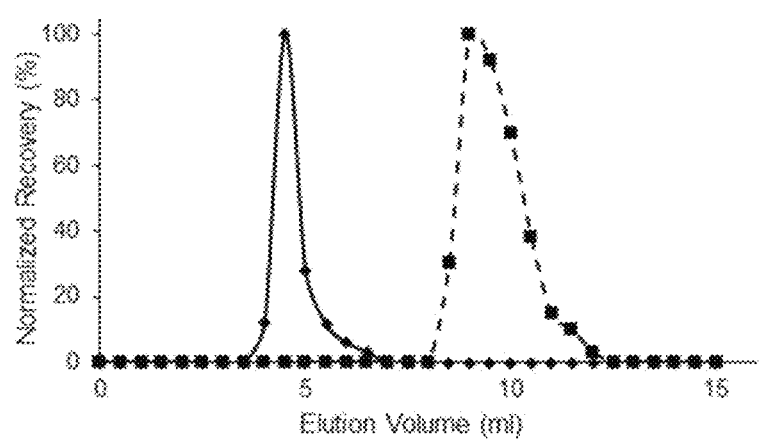
FIG. 5 illustrates Sephadex G-25 elution profiles for the mixture of 100 µL Lipo-1(1 mg/mL, based on P8-A1) and 100 µL P8-A1 (1 mg/mL). The sample was eluted with 0.9% saline solution (pH 6.5-7.0) and collected every 0.5 mL. Fractions were quantified by UV-Vis spectroscopy at a wavelength of 413 nm. The absorbance in each fraction was normalized as the percentage of the maximal absorbance in the same group. Fractions were analyzed for Lipo-1 (solid line) and P8-A1 (dash line). Note the difference in the retention times, allowing the baseline separation of free P8-A1 from liposomes under these conditions.

Pre-mature release of platinum complexes in the liposomes before reaching tumor sites should be avoided to achieve a better therapeutic index. To test their stability under physiologically relevant conditions, Lipo-1-Lipo-4 were incubated in PBS (pH=7.4) at 37° C. for 48 h. Samples were withdrawn at various time points and passed through a size exclusion column to remove any released P8-A1 (21). The purified liposomes were then quantified by UV-Vis spectroscopy and their absorbance compared with that of controls to determine the amount of drugs within the liposomes. To demonstrate that size exclusion chromatography is able to effectively separate the free P8-A1 from the liposomes, a mixture of the two forms was loaded onto a column (1 cm×10 cm) filled with Sephadex G-25. The chromatographic elution profiles of Lipo-1 and P8-A1 are shown in FIG. 5. As can be clearly seen in the elution profile, the liposome eluted from the column using 5 mL of 0.9% saline, while P8-A1 at the same concentration required about 9 mL of the same solution.

Figure 6:
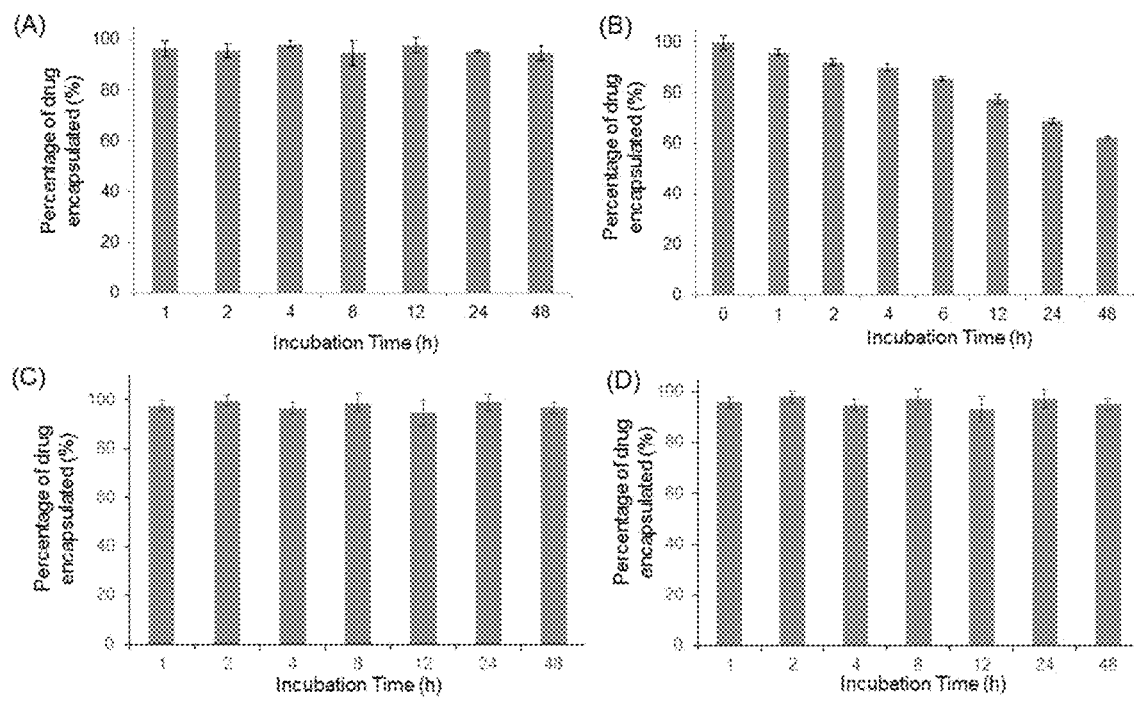
FIG. 6 illustrates in vitro leakage of P8-A1 from Lipo-1-Lipo-4 during 48 h of incubation in PBS (pH 7.4) at 37° C.
Figure 7:
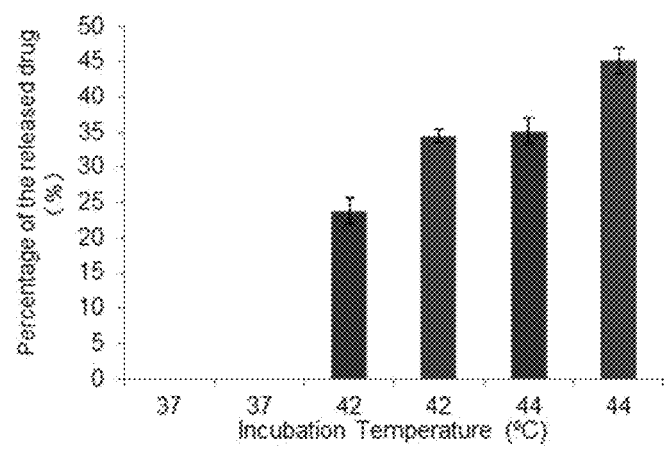
FIG. 7 illustrates in vitro release profile of P8-A1 from Lipo-1 in PBS (pH 7.4) incubated at 42° C. and 44° C. for 0.5 hour (red) and 1 hour (blue).

The stability of each formulation in PBS (pH 7.4) at 37° C. was assessed. All liposomes lacking cholesterol (Lipo-1, lipo-3 and Lipo-4) showed little leakage after 48 hours (FIG. 6), indicating excellent stability under the test conditions. This observation is consistent with a phase transition temperature greater than 37° C., which renders the lipid bilayers impermeable to the platinum complexes at physiological temperature. In addition, the electrostatic interactions of DPPG with P8-A1 may also enhance the retention of platinum complex within the lipid bilayer. On the other hand, 40% of P8-A1 was released by Lipo-2 under the same conditions, which can be explained with the incorporation of cholesterol. Cholesterol is a modulator of membrane mobility that permeabilizes the bilayer to release platinum complex at temperatures below the phase transition temperature of the bulk lipid. Moreover, since the fluidity of cholesterol-free lipid bilayers is highly sensitive to variations in temperature (20), cholesterol-free liposomes in this study would become more permeable at higher temperature. Lipo-1, mainly composed of DPPG with a phase transition temperature of 41° C., was incubated in PBS at 42° C. (FIG. 7). 24% of P8-A1 was found to be released after 30 min, and this amount increased after an incubation time of 1 hour (35%) or after elevating the temperature to 44° C. (35%). A burst release of 46% P8-A1 was detected when Lipo-1 was incubated at 44° C. for 1 h. However, it should be noted that this stability study in vitro does not faithfully mimic the in vivo behavior of liposomes. Other parameters, such as serum proteins and components of the immune system, usually facilitate decomposition of liposomes in blood, and thus release the payloads in off-target tissues.

The storage stability studies indicated that all liposomal formulations were highly stable when stored in 0.9% saline at 4° C. for at least 2 months without significant changes in size and payload content.

Example 4

Figure 8:
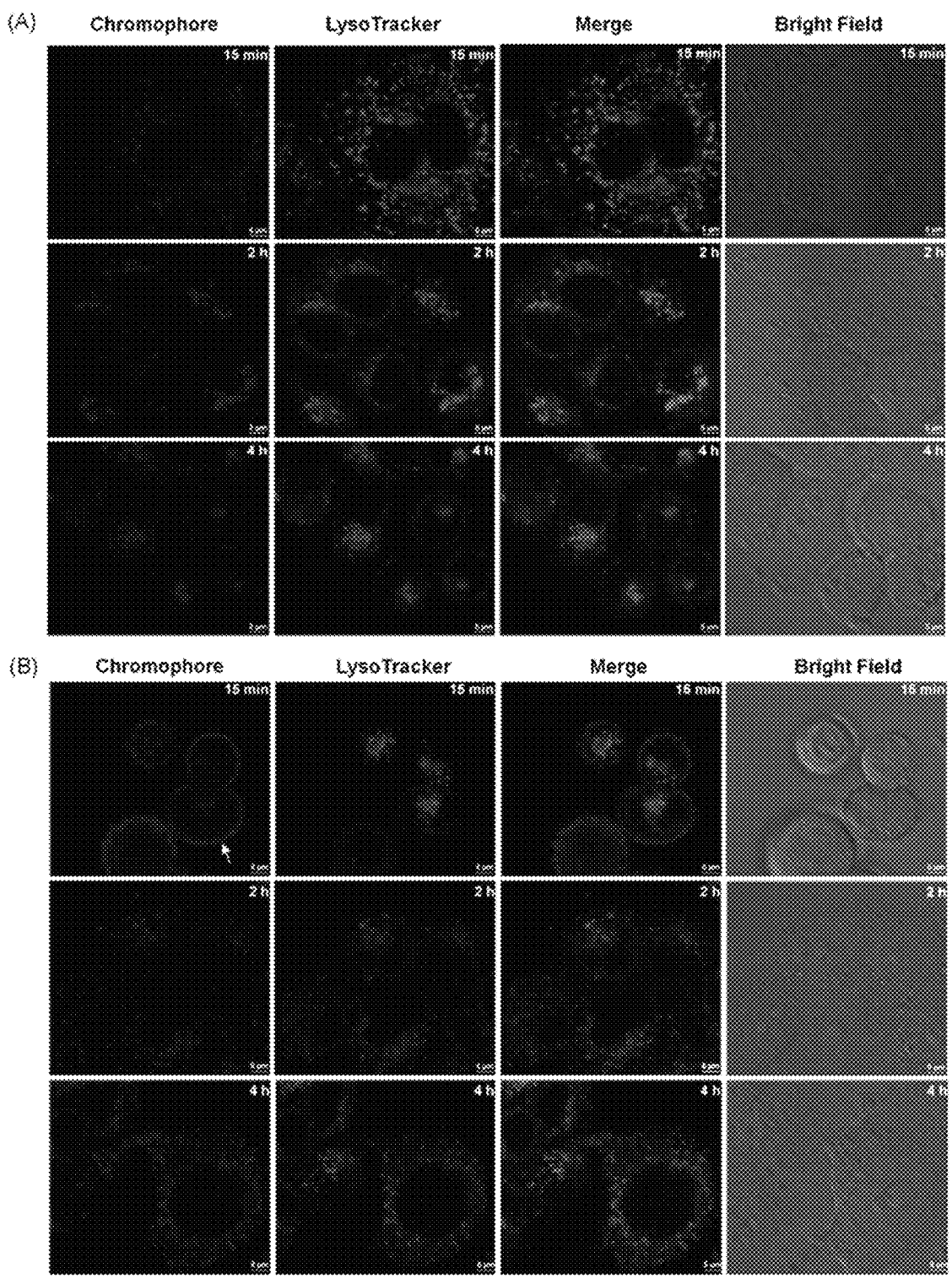
FIG. 8 illustrates confocal microscopy images of (A) P8-A1 (blue, 5 µM) and (B) Lipo-1 (blue, 5 µM) incubated in real-time of NCI-H460. Cells were co-stained with LysoTracker Red. Scale bars represent a distance of 5 µm. White arrow indicates that Lipo-1 internalize into cells through a membrane-fusion mechanism.
Figure 11:
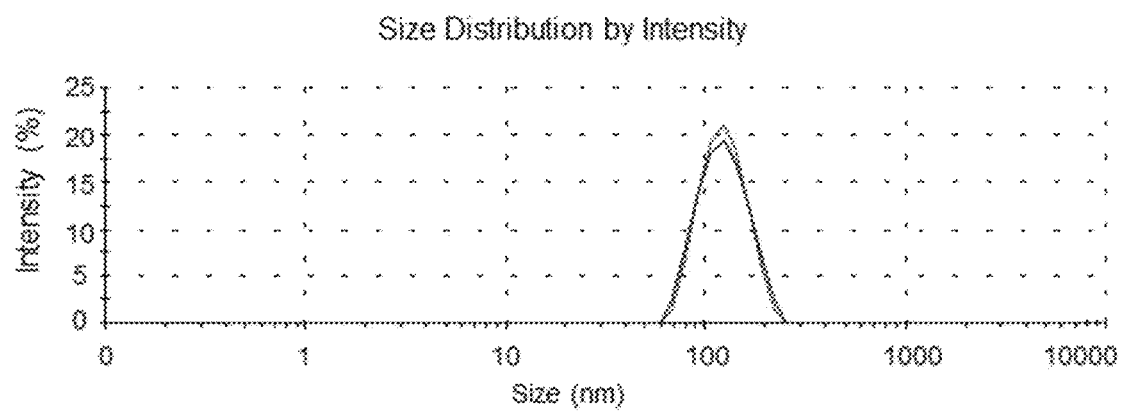
FIG. 11 illustrates size distribution of Lipo-1 determined by DLS.
Figure 12:
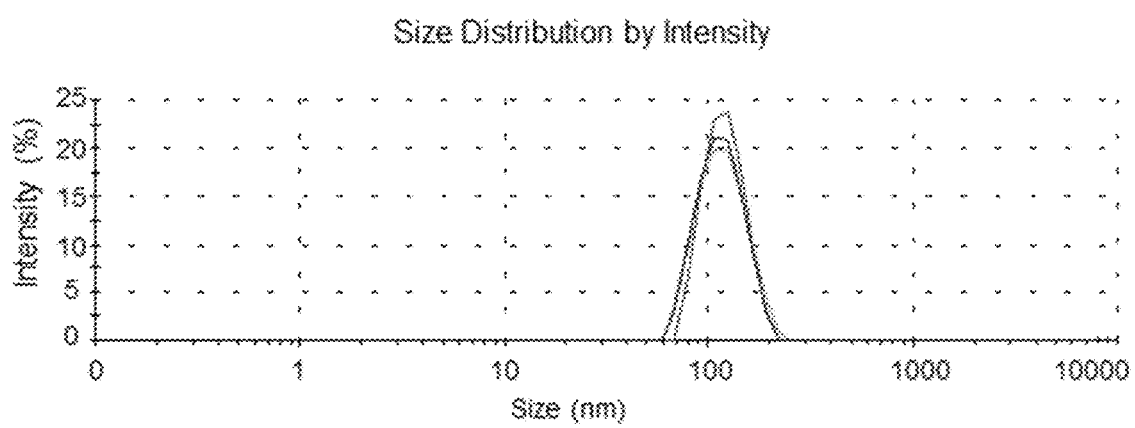
FIG. 12 illustrates size distribution of Lipo-2 determined by DLS.
Figure 13:
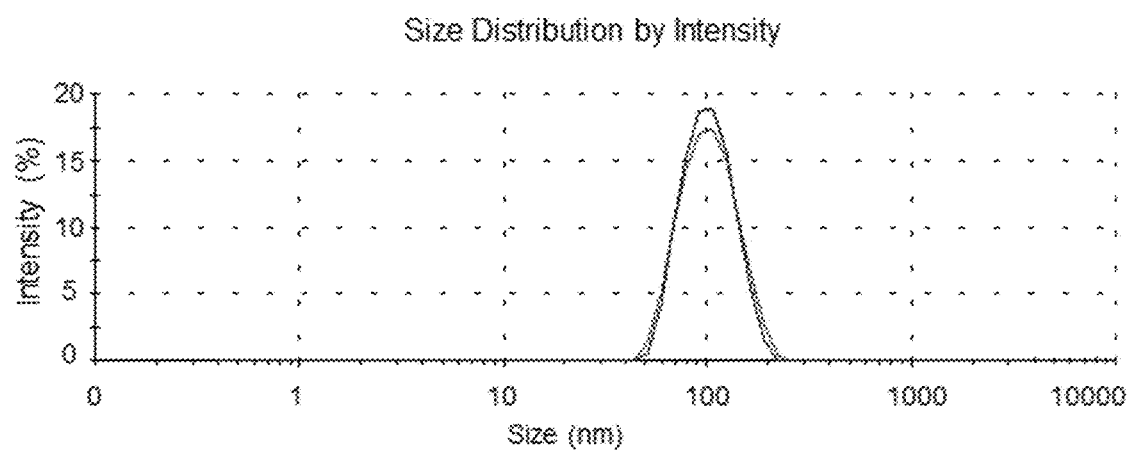
FIG. 13 illustrates size distribution of Lipo-3 determined by DLS.
Figure 14:
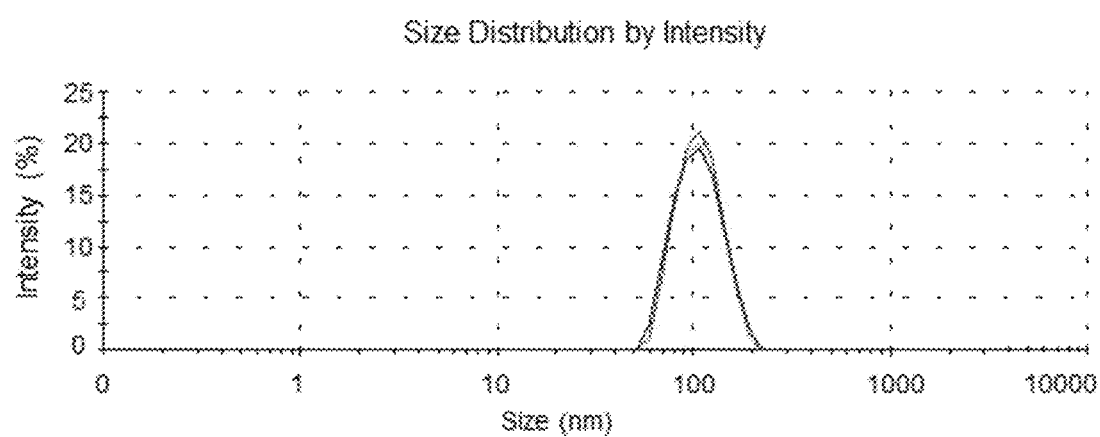
FIG. 14 illustrates size distribution of Lipo-4 determined by DLS.
Figure 15:
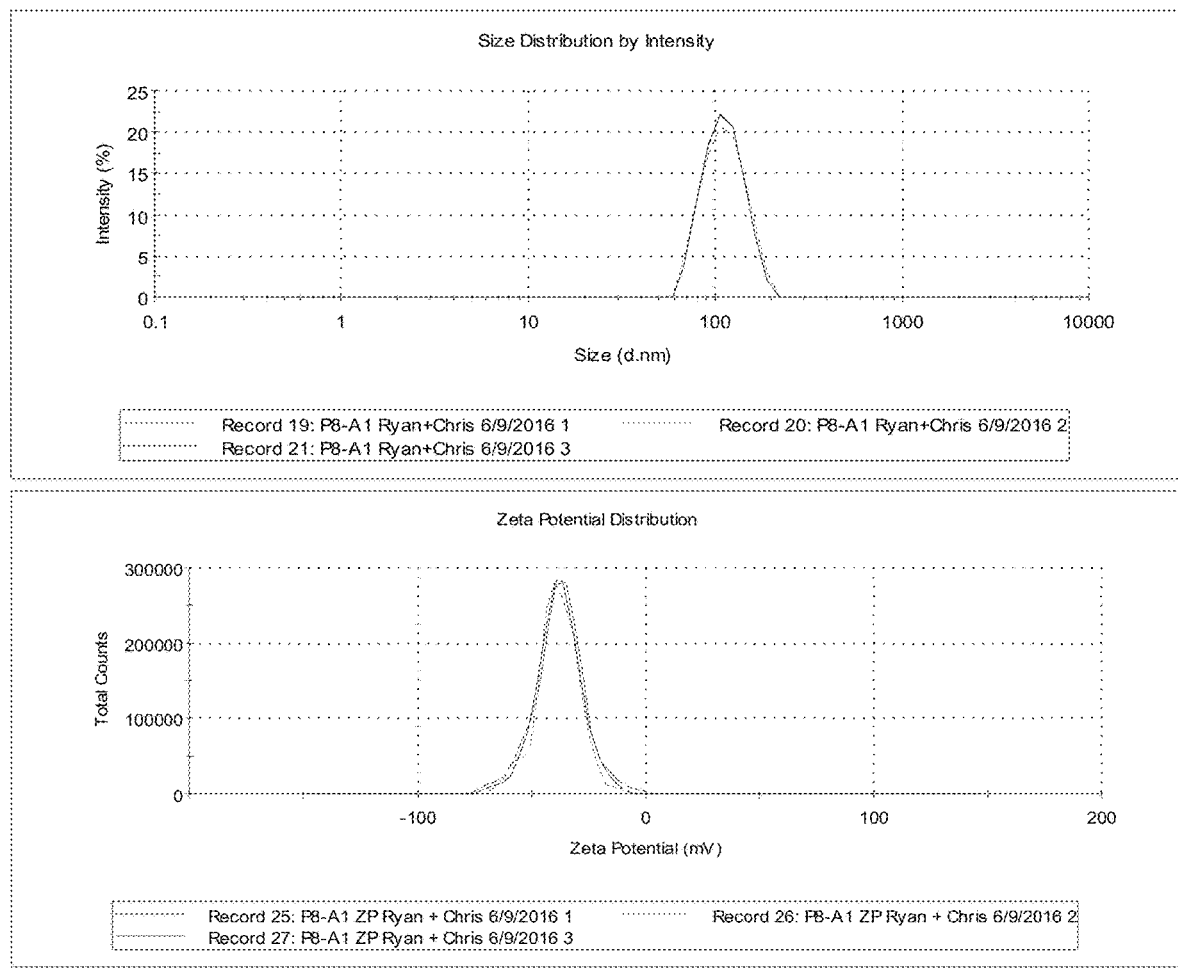
FIG. 15 illustrates characterization of Lipo4*-P8-A1 by DLS (top panel: hydrodynamic diameter; bottom panel: zeta-potential).

Uptake of Liposomal Formulations into Cancer Cells and Subcellular Drug Localization Because of the intrinsic blue fluorescence of the 9-aminoacridine, cellular uptake and intracellular accumulation of P8-A1 in liposomes can be directly observed using confocal fluorescent microscopy (22). P8-A1 (5 µM) and Lipo-1 (containing 5 µM P8-A1) were incubated with non-small cell lung cancer NCI-H460 cells. Dosed cells were then co-stained with Lyso Tracker (red fluorescence) to study the accumulation of the P8-A1 in acidic lysosomes prior to the microscopy sessions. As shown in FIGS. 8(A) and (B), higher levels of intracellular blue fluorescence were detected in the Lipo-1 treated cells relative to cells dosed with P8-A1, indicating that the liposomes facilitate the uptake of P8-A1 into cells. However, it is difficult to quantify the differential uptake, since significant quenching of the fluorescence occurs when the 9-aminoacridine chromophore is intercalated between DNA base pairs in the nucleus (23). After incubation for 4 hours, P8-A1, consistent with our previous findings (23), was found to localize to the nucleoli in both groups. Nucleolar localization of free P8-A1 was observed after 2-hour incubation (FIG. 8(A)), which was significantly faster than liposomes, suggesting that they may have different mechanisms of cellular uptake.

A high degree of co-localization of P8-A1 with Lyso Tracker was found in the cells incubated with free P8-A1 for only 15 min, confirming rapid accumulation of platinum complexes in the lysosomes after entering into cancer cells. The lysosomotropic properties of PAs can be attributed to their cationic nature, which may favor interactions with the negatively charged lysosomal membranes to facilitate sequestration (24). The lysosomes seem to localize to the perinuclear region and slowly release P8-A1 into the nucleus. Lack of effective lysosomal escape is the primary reason for drug resistance observed for lysosomotropic agents if their major biological targets are located in the nucleus (25). This may be a shortcoming of P8-A1 in resistant cancer cells. To induce apoptosis in these cells, rapid accumulation in the nucleus is beneficial.

By contrast, Lipo-1 seemed to internalize into cells through a membrane-fusion mechanism presumably as a result of the presence of the fusogenic phospholipid DPPG (7). Strikingly, a ring-shaped intense blue fluorescence is observed around the membranes of cells treated with Lipo-1 after 15 minutes of incubation (FIG. 8B). The membrane-associated liposomes persist after 2 hours, indicating that the uptake of Lipo-1, unlike that of free P8-A1, is a relatively slower process. After fusing with the cell membrane, Lipo-1 releases loaded P8-A1 directly into the cytosol, as clearly evidenced by the blue punctuations that does not co-localize with the lysosomes stained by red fluorescent Lyso Tracker. Accumulation of P8-A1 to the lysosomes was also observed in these cells, but to a lesser extent in cells treated with free drug at the same time points (FIG. 9). Since liposomes facilitate the delivery of a large amount of P8-A1 directly into the cytosols, P8-A1 did not get sequestered by the lysosomes. Elevated levels of blue fluorescence in vesicles distinct from the red-fluorescent lysosomes, appeared in the perinuclear region of cells after incubation with Lipo-1 for 4 hours (FIG. 9). This observation suggests that a high concentration of P8-A1 is able to accumulate close to the nucleus, which may help the drug to reach its target and evade cytosolic detoxification.

Liposome-induced lysosomal shuttling of payload to the nucleus protects PAs from cytosolic platinum detoxification caused by mechanisms such as Pt sequestration by glutathione, which confer resistance to platinum drugs. Since dicationic PAs are unable to enter cancer cells unless these express cation transporters, the observed mechanism of membrane fusion provides an important alternative mechanism of cellular uptake and strategy of sensitizing cancers that would be otherwise resistant to PAs.

Example 5

Acute Toxicity Studies of Liposomal P8-A1 (Dose Escalation)

To evaluate the acute toxicity of the formulations prepared in this study, Lipo-1-Lipo-4 were administered intravenously to female Swiss-Webster mice. The maximum tolerated dose (MTD) was determined based on clinical signs of toxicity, such as piloerection, weight loss, and lethargy. Free P8-A1 was tested as a control under identical conditions. P8-A1, in agreement with previous results (1), exhibited systemic toxicity in mice models with a maximum tolerated dose (MTD) of 0.4 mg/kg for a single dose or multiple doses (q4dx4). For the formulations, a significant increase in MTD was observed with Lipo-2 (0.8 mg/kg), which contains cholesterol in the bilayer, whereas Lipo-1, Lipo-3 and Lipo-4 were found to have the same MTD as the free drug. However, unlike P8-A1 the most recently tested formulation, Lipo4*-P8-A1, which was generated and purified by a modified procedure, resulted in no weight loss at the same dose (0.4 mg/kg) in test animals when administered i.v. This observation is consistent with Lipo4*-P8-A1 being tolerated better than P8-A1 by the treated mice, indicating a higher MTD.

Example 6

In Vivo Antitumor Efficacy

A549 (NSCLC, human adenocarcinoma) was selected as the xenograft model (athymic nude mice) to test the efficacy of P8-A1, Lipo4-encapsulated P8-A1, and cisplatin, standard of care for NSCLC. Before a decision was made in favor of this model, P8-A1 was tested in A549 cells using a colorimetric cell proliferation assay, in which the derivative was highly active with an $IC_{50}$ value of 3.9 nM. The in vivo treatment schedule consisted of i.v. injections (see caption of FIG. 10 for details). Test animals were monitored for weight loss and signs of toxicity three times a week. Data analysis for weight and tumor volumes was done with the Student's t-test. Only P values of less than 0.05 were considered as statistically significant. The results of two representative studies are presented in FIG. 10. These can be summarized as follows:

Study A (FIG. 10A, B)

Treatment details: Lipo4-P8-A1, control, administered q4dx4, i.v. @ 0.4 mg/kg, n=10
Tumor growth inhibition: 65% (P<0.05) relative to vehicle-treated control
Weight loss: 22% on day 41, reversible, no other signs of toxicity Study B (FIG. 10C, D)

Treatment details: P8-A1, Lipo4*-P8-A1, cisplatin, control, administered q4d, i.v., n=8
There is stat. significant difference in tumor volumes between control (Group 1) and P8-A1 (group 3) and Lipo4*-P8-A1 (Groups 4 and 5), P<0.05

P8-A1 and Lipo4*-P8-A1 show antitumor efficacy (growth inhibition of 51%), there is no significant difference in activity between the two treatment groups
Liposomal formulation did not enhance antitumor efficacy of P8-A1
Size of tumors in cisplatin-treated mice is not significantly reduced relative to vehicle-treated controls. Cisplatin, the clinical standard of care, does not show efficacy!
Only Group 3 (free P8-A1) shows statistically significant weight loss (~20%) relative to Group 1 (control), but the weight loss appears to be (partially) reversible. Conclusion: liposomal encapsulation reduces the toxicity of P8-A1 when the formulation is administered at the same dose (equivalent dose of P8-A1). The refined formulation, Lipo4*-P8-A1, which can be considered free of unencapsulated P8-A1 (e.g., drug electrostatically bound to the negatively charged lipid head groups lipids on the outer surface of the liposomes), shows improved tolerability.

In all xenograft studies performed, tumors and selected organs were recovered from necropsied test animals. In one of the studies on formulations of Lipo1-P8-A1 and Lipo2-P8-A1, residual platinum levels were determined by inductively-coupled plasma mass spectrometry (ICP-MS, Table 3) to assess if differences in the tissue distribution exist between the free drug and the formulations.

TABLE 3

| | Average ng Pt in Organs[a] | | | |
|---|---|---|---|---|
| | Liver | Kidneys | Lungs | Spleen |
| control | 0.481 ± 0.200 | 0.0278 ± 0.0001[b] | 0.0463 ± 0.009 | 0.0278 ± 0.0001[b] |
| P8-A1 | 1316 ± 226 | 175 ± 34 | 5.03 ± 0.585 | 10.04 ± 1.53 |
| Lipo-1 | 617 ± 180* | 55.9 ± 19.8* | 2.31 ± 0.31* | 28.4 ± 8.2 |
| Lipo-2 | 976 ± 183 | 151 ± 41 | 5.38 ± 0.72 | 97.9 ± 10.6 |

[a]Recovered from euthanized mice 14 days after administration of the last dose. Data are ng Pt per organ ± SEM determined for 5 organs per group by ICP-MS.
[b]Limit of detection.
*P < 0.05.

Lipo-1 produced significantly lower platinum levels in liver, kidneys, and lungs than unencapsulated P8-A1. It also appeared that encapsulated P8-A1 was delivered more efficiently to large tumors, which faithfully mimic the poor lymphatic drainage and defective blood vessels in the tumor tissue. This observation is consistent with enhanced accumulation of the liposomes in tumor tissue caused by the EPR effect.

The foregoing non-limiting examples and embodiments are described to illustrate certain aspects of the present invention. Those skilled in the art will understand that various changes or modifications may be made without departing from the spirit and scope of the invention. All references mentioned herein are incorporated by reference in their entirety.

REFERENCES

1. Ma, Z., Choudhury, J. R., Wright, M. W., Day, C. S., Saluta, G., Kucera, G. L. and Bierbach, U. (2008) A non-cross-linking platinum-acridine agent with potent activity in non-small-cell lung cancer. *Journal of Medicinal Chemistry*, 51, 7574-7580.
2. Bozzuto, G. and Molinari, A. (2015) Liposomes as nanomedical devices. *International Journal of Nanomedicine*, 10, 975-999.

3. Barenholz, Y. (2012) Doxil (R)—The first FDA-approved nano-drug: Lessons learned. *Journal of Controlled Release*, 160, 117-134.
4. Cern, A., Golbraikh, A., Sedykh, A., Tropsha, A., Barenholz, Y. and Goldblum, A. (2012) Quantitative structure—property relationship modeling of remote liposome loading of drugs. *Journal of Controlled Release*, 160, 147-157.
5. Allen, T. M. and Cullis, P. R. (2013) Liposomal drug delivery systems: From concept to clinical applications. *Advanced Drug Delivery Reviews*, 65, 36-48.
6. Kale, A. A. and Torchilin, V. P. (2007) "Smart" drug carriers: PEGylated TATp-Modified pH-Sensitive Liposomes. *Journal of Liposome Research*, 17, 197-203.
7. Stathopoulos, G. P. and Boulikas, T. (2012) Lipoplatin formulation review article. *Journal of drug delivery*, 2012, 581363-581363.
8. Graham, L. A., Suryadi, J., West, T. K., Kucera, G. L. and Bierbach, U. (2012) Synthesis, Aqueous Reactivity, and Biological Evaluation of Carboxylic Acid Ester-Functionalized Platinum-Acridine Hybrid Anticancer Agents. *Journal of Medicinal Chemistry*, 55, 7817-7827.
9. Ding, S., Pickard, A. J., Kucera, G. L. and Bierbach, U. (2014) Design of Enzymatically Cleavable Prodrugs of a Potent Platinum-Containing Anticancer Agent. *Chemistry—A European Journal*, 20, 16164-16173.
10. Allen, C., Dos Santos, N., Gallagher, R., Chiu, G. N. C., Shu, Y., Li, W. M., Johnstone, S. A., Janoff, A. S., Mayer, L. D., Webb, M. S. et al. (2002) Controlling the physical behavior and biological performance of liposome formulations through use of surface grafted poly(ethylene glycol). *Bioscience Reports*, 22, 225-250.
11. Torchilin, V. P., Omelyanenko, V. G., Papisov, M. I., Bogdanov, A. A., Trubetskoy, V. S., Herron, J. N. and Gentry, C. A. (1994) Poly(ethylene glycol) on the liposome surface-on the mechanism of polymer-coated liposome longevity. *Biochimica Et Biophysica Acta-Biomembranes*, 1195, 11-20.
12. Briuglia, M.-L., Rotella, C., McFarlane, A. and Lamprou, D. A. (2015) Influence of cholesterol on liposome stability and on in vitro drug release. *Drug Delivery and Translational Research*, 5, 231-242.
13. Dos Santos, N., Mayer, L. D., Abraham, S. A., Gallagher, R. C., Cox, R. A. K., Tardi, P. G. and Bally, M. B. (2002) Improved retention of idarubicin after intravenous injection obtained for cholesterol-free liposomes. *Biochimica Et Biophysica Acta-Biomembranes*, 1561, 188-201.
14. Colletier, J.-P., Chaize, B., Winterhalter, M. and Fournier, D. (2002) Protein encapsulation in liposomes: efficiency depends on interactions between protein and phospholipid bilayer. *BMC biotechnology*, 2, 9-9.
15. Costa, A. P., Xu, X. and Burgess, D. J. (2014) Freeze-Anneal-Thaw Cycling of Unilamellar Liposomes: Effect on Encapsulation Efficiency. *Pharmaceutical Research*, 31, 97-103.
16. Dos Santos, N., Allen, C., Doppen, A.-M., Anantha, M., Cox, K. A. K., Gallagher, R. C., Karlsson, G., Edwards, K., Kenner, G., Samuels, L. et al. (2007) Influence of poly(ethylene glycol) grafting density and polymer length on liposomes: Relating plasma circulation lifetimes to protein binding. *Biochimica Et Biophysica Acta-Biomembranes*, 1768, 1367-1377.
17. Burger, K. N., Staffhorst, R. W., de Vijlder, H. C., Velinova, M. J., Bomans, P. H., Frederik, P. M. and de Kruijff, B. (2002) Nanocapsules: lipid-coated aggregates of cisplatin with high cytotoxicity. *Nature Medicine*, 8, 81-84.
18. Zalba, S., Navarro, I., Troconiz, I. F., Tros de Ilarduya, C. and Garrido, M. J. (2012) Application of different methods to formulate PEG-liposomes of oxaliplatin: Evaluation in vitro and in vivo. *European Journal of Pharmaceutics and Biopharmaceutics*, 81, 273-280.
19. Shmeeda, H., Amitay, Y., Tzemach, D., Gorin, J. and Gabizon, A. (2013) Liposome encapsulation of zoledronic acid results in major changes in tissue distribution and increase in toxicity. *Journal of Controlled Release*, 167, 265-275.
20. Ickenstein, L. M., Arfvidsson, M. C., Needham, D., Mayer, L. D. and Edwards, K. (2003) Disc formation in cholesterol-free lippsornes during phase transition. *Biochimica Et Biophysica Acta-Biomembranes*, 1614, 135-138.
21. $R_1$ viere, K., Kieler-Ferguson, H. M., Jerger, K. and Szoka, F. C., Jr. (2011) Anti-tumor activity of liposome encapsulated fluoroorotic acid as a single agent and in combination with liposome irinotecan. *Journal of Controlled Release*, 153, 288-296.
22. Pickard, A. J., Liu, F., Bartenstein, T. F., Haines, L. G., Levine, K. E., Kucera, G. L. and Bierbach, U. (2014) Redesigning the DNA-Targeted Chromophore in Platinum-Acridine Anticancer Agents: A Structure-Activity Relationship Study. *Chemistry—A European Journal*, 20, 16174-16187.
23. Ding, S., Qiao, X., Suryadi, J., Marrs, G. S., Kucera, G. L. and Bierbach, U. (2013) Using Fluorescent Post-Labeling To Probe the Subcellular Localization of DNA-Targeted Platinum Anticancer Agents. *Angewandte Chemie-International Edition*, 52, 3350-3354.
24. He, C., Lu, K., Liu, D. and Lin, W. (2014) Nanoscale Metal-Organic Frameworks for the Co-Delivery of Cisplatin and Pooled siRNAs to Enhance Therapeutic Efficacy in Drug-Resistant Ovarian Cancer Cells. *Journal of the American Chemical Society*, 136, 5181-5184.
25. Shete, H. K., Prabhu, R. H. and Patravale, V. B. (2014) Endosomal Escape: A Bottleneck in Intracellular Delivery. *Journal of Nanoscience and Nanotechnology*, 14, 460-474.

What is claimed is:
1. A lipid composition comprising
(a) a metallopharmaceutical of Formula A:

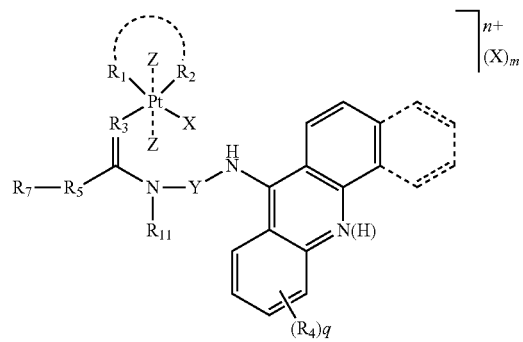

Formula A wherein,
each X is independently halo, —OC(O)$R_9$, nitrate or sulfate;
$R_1$ and $R_2$ are amino groups or together with the platinum atom to which they are attached, $R_1$ and $R_2$ form the ring —$NH_2$—$(CH_2)_v$—$NH_2$— wherein v is 1, 2 or 3, or $R_1$ and $R_2$ together can be any of the following groups a-h, or $R_1$ and $R_2$ independently can be any of the following groups i-m;

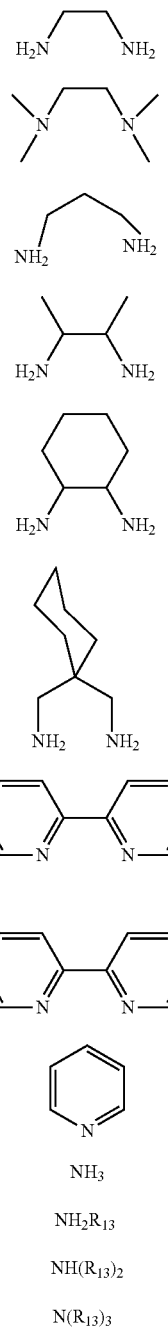

a b c d e f g h i  pyridine j  $NH_3$ k  $NH_2R_{13}$ l  $NH(R_{13})_2$ m  $N(R_{13})_3$ wherein A is H, —$CH_3$, —$OCH_3$, $CF_3$, or $NO_2$;
$R_{13}$ is independently $C_1$-$C_6$alkyl;
$R_3$ is —$N(R_6)$—, wherein $R_6$ is hydrogen or $C_1$-$C_6$alkyl;
$R_4$ is independently an amino, a nitro, —$NHC(O)(R_{10})$, —$C(O)NHR_{10}$, or halo;
$R_{10}$ is hydrogen, $C_{1-6}$ alkyl, phenyl, naphthyl, $C_{3-6}$ cycloalkyl, norhornyl, or adamantyl;
q is 0, 1, or 2;
$R_5$ is a direct bond, or $C_1$-$C_6$alkylene;
or $R_5$ and X together with the atoms to which they are attached form a 6- or 7-membered ring, wherein said 6- or 7-membered ring contains a linking group —C(O)O— or —OC(O);
R7 is hydrogen, or methyl;
$R_9$ is hydrogen, $C_{1-6}$ alkyl, phenyl, naphthyl, $C_{3-6}$ cycloalkyl, norbornyl, or adamantyl;
$R_{11}$ is hydrogen or $C_1$-$C_6$alkyl;
n is 1, 2, 3 or 4;
m is 1, 2, 3 or 4;
Y is $C_1$-$C_6$alkylene; and
Z is an optional additional axial ligand selected from the group consisting of halide, $OH^-$, $CH_3COO^-$, and $RCOO^-$, wherein R is a substituted or unsubstituted alkyl or aryl; and (b) an encapsulating lipid mixture, consisting essentially of
i. a negatively charged lipid;
ii. a phosphatidylcholine;
iii. a polyethylene glycol-containing lipid;
wherein the negatively charged lipid is more than about 20 mol % in the lipid mixture; further wherein the metallopharmaceutical ranges from about 2% to about 20% by weight in the composition, and wherein the lipid composition is substantially free from cholesterol, and wherein the encapsulating lipid mixture is configured to enable delivery of a therapeutically effective amount of the metallopharmaceutical.

2. The lipid composition of claim 1, wherein the metallopharmaceutical is selected from the group consisting of

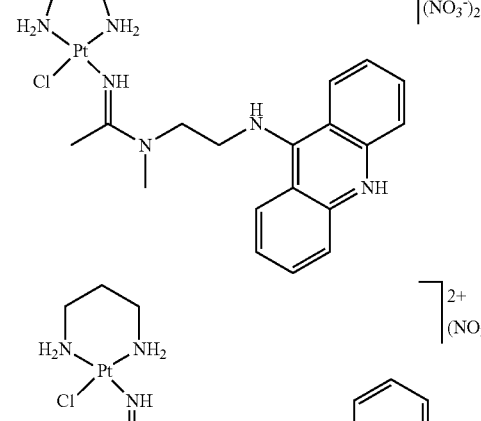

and

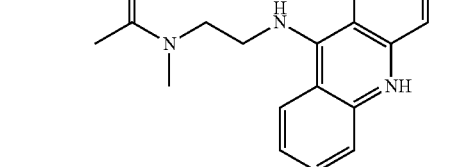

3. The lipid composition of claim 1, wherein the negatively charged lipid is 1,2-dihexadecanoyl-sn-glycero-3-phospho-(1'-rac-glycerol) (DPPG).

4. The lipid composition of claim 1, wherein the negatively charged lipid is more than about 60 mol % in the lipid mixture.

5. The lipid composition of claim 1, wherein the phosphatidylcholine is 1,2-Distearoyl-sn-glycero-3-phosphoethanolamine (DSPE).

6. The lipid composition of claim 1, wherein the phosphatidylcholine ranges from about 5 mol % to about 25 mol % in the mixture.

7. The lipid composition of claim 1, wherein the polyethylene glycol-containing lipid is mPEG-1,2-Distearoyl-sn-glycero-3-phosphoethanolamine (mPEG-DSPE).

8. The lipid composition of claim 1, wherein the polyethylene glycol-containing lipid ranges from about 0.5 mol % to about 15 mol % in the mixture.

9. The lipid composition of claim 1, wherein the lipid mixture is a single bilayer of lipids encapsulating the metallopharmaceutical.

10. The lipid composition of claim 1, which has an average diameter of less than about 120 nm.

11. A method of treating cancer in a subject, comprising administering the lipid composition of claim 1 to the subject in need, wherein the cancer is selected from the group consisting of lung cancer, colon cancer, breast cancer, pancreatic cancer, melanoma, kidney cancer, and prostate cancer.

12. A method of manufacturing the lipid composition of claim 1, comprising (a) providing a lipid mixture consisting essentially of
   i. a negatively charged lipid;
   ii. a phosphatidylcholine; and
   iii. a polyethylene glycol-containing lipid;
   wherein the lipid mixture is substantially free from cholesterol;
   (b) mixing the liquid mixture with a solution comprising the metallopharmaceutical of Formula A to form a liposomal suspension, wherein the ratio by weight between the metallopharmaceutical and the lipid mixture ranges from about 0.01 to about 0.5, and wherein the liposomal suspension is configured to enable delivery of a therapeutically effective amount of the metallopharmaceutical.

13. The method of claim 12, wherein the ratio ranges from about 0.03 to about 0.07.

14. The method of claim 12, wherein step (a) comprises adding the lipid mixture to a solvent and removing the solvent to form a film.

15. The method of claim 12, wherein the solution in step (b) is a saline solution further comprising a cryoprotectant.

16. The method of claim 15, wherein the cryoprotectant is a saccharide selected from the group consisting of mannitol, sucrose, glucose, and glucose.

17. The method of claim 15, wherein the cryoprotectant ranges from about 1% to about 15% by weight in the solution.

18. The method of claim 12, wherein step (b) further comprises cooling and heating the liposomal suspension.

19. The method of claim 15, wherein step (b) further comprises extruding the liposomal suspension through a membrane.

20. The lipid composition of claim 1, wherein the negatively charged lipid is DPPG, the phosphatidylcholine is 1,2-Distearoyl-sn-glycero-3-phosphoethanolamine (DSPE) and the polyethylene glycol-containing lipid is mPEG-DSPE.

21. The lipid composition of claim 1, wherein the metallopharmaceutical molecule is about 2% in the composition.

22. The lipid composition of claim 1, wherein the metallopharmaceutical molecule is about 20% in the composition.

23. The lipid composition of claim 1, wherein Z is present in the metallopharmaceutical.

* * * * *